US012336953B2

(12) United States Patent
Mooney et al.

(10) Patent No.: US 12,336,953 B2
(45) **Date of Patent: *Jun. 24, 2025**

(54) SYSTEMS AND METHODS FOR AN ACTIVE EXOSKELETON WITH LOCAL BATTERY

(71) Applicant: Dephy, Inc., Boxborough, MA (US)

(72) Inventors: Luke Mooney, Boxborough, MA (US); Jean-François Duval, Boxborough, MA (US); Nicholas Benz, Boxborough, MA (US); Jonathan Cummings, Boxborough, MA (US); Matthew Mooney, Boxborough, MA (US)

(73) Assignee: Dephy, Inc.

( * ) Notice: Subject to any disclaimer, the term of this patent is extended or adjusted under 35 U.S.C. 154(b) by 0 days.

This patent is subject to a terminal disclaimer.

(21) Appl. No.: 18/244,802

(22) Filed: Sep. 11, 2023

(65) Prior Publication Data

US 2024/0216208 A1 Jul. 4, 2024

Related U.S. Application Data

(63) Continuation of application No. 17/526,454, filed on Nov. 15, 2021, now Pat. No. 11,752,061, which is a (Continued)

(51) Int. Cl.

*A61H 3/00* (2006.01)
*A61F 5/00* (2006.01)

(Continued)

(52) U.S. Cl.

CPC ................ *A61H 3/00* (2013.01); *A61F 5/00* (2013.01); *B25J 9/0006* (2013.01); *B25J 9/16* (2013.01);

(Continued)

(58) Field of Classification Search

CPC . B25J 9/0006; B25J 19/005; B25J 9/16; B25J 9/0009; B25J 9/161; A61H 3/00;

(Continued)

(56) References Cited

U.S. PATENT DOCUMENTS

| | | | |
|---|---|---|---|
| 2,477,591 | A | 8/1949 | Follis |
| 2,516,872 | A | 8/1950 | Hauser et al. |

(Continued)

FOREIGN PATENT DOCUMENTS

| | | | |
|---|---|---|---|
| CA | 2937610 | A1 | 7/2009 |
| CN | 202679044 | U | 1/2013 |

(Continued)

OTHER PUBLICATIONS

Sanz-Morère et al., A Knee-Ankle-Foot Orthosis to Assist the Sound Limb of Transfemoral Amputees, 2019, IEEE, p. 38-48 (Year: 2019).*

(Continued)

*Primary Examiner* — Mcdieunel Marc
(74) *Attorney, Agent, or Firm* — Foley & Lardner LLP

(57) ABSTRACT

An apparatus for a battery-powered active exoskeleton boot includes a shin pad and one or more housings. The one or more housings enclose electronic circuitry and an electric motor. The apparatus includes a battery holder coupled to the shin pad and located below the knee of the user and above the one or more housings enclosing the electronic circuitry. The apparatus includes a battery module removably affixed to the battery holder and comprising a first power connector that electrically couples to a second power connector located in the battery holder while attached to the battery holder to provide electric power to the electronic circuitry and the electric motor. The apparatus includes an output shaft coupled to the electric motor. The electronic circuitry controls delivery of power from the battery module (Continued)

to the electric motor to generate torque about the axis of rotation of the ankle joint of the user.

20 Claims, 27 Drawing Sheets

Related U.S. Application Data continuation of application No. 17/022,982, filed on Sep. 16, 2020, now Pat. No. 11,173,093.

(51) Int. Cl.
*B25J 9/00* (2006.01)
*B25J 9/16* (2006.01)
*B25J 19/00* (2006.01)
*H02P 1/00* (2006.01)

(52) U.S. Cl.
CPC .............. *B25J 19/005* (2013.01); *H02P 1/00* (2013.01); *B25J 9/0009* (2013.01)

(58) Field of Classification Search
CPC .... A61H 2201/1642; A61H 2201/5097; A61H 2201/164; A61H 2201/1215; A61H 2201/1207; A61H 2201/5069; A61H 2201/5007; A61H 2201/5079; A61H 2201/5082; A61H 1/0266; A61H 2201/0111; A61H 2201/5061; A61H 2003/007; A61H 2201/165; A61H 2201/5084; A61F 5/00; H02P 1/00; Y02E 60/10
See application file for complete search history.

(56) References Cited

U.S. PATENT DOCUMENTS 2,573,698 A 11/1951 Ellery
3,064,644 A 11/1962 Patterson
5,014,690 A 5/1991 Hepburn et al.
5,490,831 A 2/1996 Myers et al.
5,685,830 A 11/1997 Bonutti
6,299,588 B1 10/2001 Fratrick
6,872,187 B1 3/2005 Stark et al.
7,153,242 B2 12/2006 Goffer
7,431,737 B2 10/2008 Ragnarsdottir et al.
7,531,006 B2 5/2009 Clausen et al.
7,628,766 B1 12/2009 Kazerooni et al.
7,811,333 B2 10/2010 Jonsson et al.
8,114,168 B2 2/2012 Olafsson et al.
8,435,309 B2 5/2013 Gilbert et al.
8,516,918 B2 8/2013 Jacobsen et al.
8,585,620 B2 11/2013 Mcbean et al.
8,597,369 B2 12/2013 Hansen et al.
8,734,528 B2 5/2014 Herr et al.
8,764,850 B2 7/2014 Hansen et al.
8,784,350 B2 7/2014 Cohen
8,790,282 B2 7/2014 Jung et al.
8,801,802 B2 8/2014 Oddsson et al.
8,864,846 B2 10/2014 Herr et al.
8,870,801 B2 10/2014 Tomiyama et al.
8,870,967 B2 10/2014 Herr et al.
9,017,419 B1 4/2015 Landry et al.
9,066,819 B2 6/2015 Gramnaes
9,078,774 B2 7/2015 Jonsson et al.
9,198,821 B2 12/2015 Unluhisarcikli et al.
9,333,097 B2 5/2016 Herr et al.
9,339,397 B2 5/2016 Herr et al.
9,345,608 B2 5/2016 Phillips
9,351,900 B2 5/2016 Walsh et al.
9,480,618 B2 11/2016 Hsiao-Wecksler et al.
9,539,117 B2 1/2017 Herr et al.
9,554,922 B2 1/2017 Casler et al.
9,662,262 B2 5/2017 Hollander et al.
9,693,883 B2 7/2017 Herr et al.
9,707,104 B2 7/2017 Clausen
9,737,419 B2 8/2017 Herr et al.
9,808,390 B2 11/2017 Caires et al.
9,839,552 B2 12/2017 Han et al.
9,872,782 B2 1/2018 Herr et al.
9,907,722 B2 3/2018 Aguirre-Ollinger et al.
9,925,071 B2 3/2018 Langlois et al.
9,980,873 B2 5/2018 Tung et al.
10,195,057 B2 2/2019 Clausen
10,251,762 B2 4/2019 Langlois
10,307,271 B2 6/2019 Holgate et al.
10,307,272 B2 6/2019 Herr et al.
10,335,294 B2 7/2019 Huang et al.
10,369,023 B2 8/2019 Simon et al.
10,405,996 B2 9/2019 Langlois
10,406,002 B2 9/2019 Herr et al.
10,426,637 B2 10/2019 Tong et al.
10,463,561 B2 11/2019 Zhang et al.
10,485,681 B2 11/2019 Herr et al.
10,532,000 B1 1/2020 De Sapio et al.
10,537,449 B2 1/2020 Han et al.
10,561,563 B2 2/2020 Herr et al.
10,576,620 B1 3/2020 Chou et al.
11,389,367 B2 7/2022 Mooney et al.
11,413,210 B2 8/2022 Contreras-Vidal et al.
11,752,061 B2 * 9/2023 Mooney .................... B25J 9/16 623/7
11,918,536 B2 3/2024 Mooney et al.
2006/0167564 A1 7/2006 Flaherty et al.
2006/0184280 A1 8/2006 Oddsson et al.
2007/0225620 A1 9/2007 Carignan et al.
2009/0030530 A1 1/2009 Martin
2009/0210093 A1 8/2009 Jacobsen et al.
2009/0222105 A1 9/2009 Clausen et al.
2010/0049333 A1 2/2010 Endo et al.
2010/0130894 A1 5/2010 Ikeuchi
2010/0198124 A1 8/2010 Bhugra
2010/0231206 A1 9/2010 Kobayashi
2011/0066088 A1 3/2011 Little et al.
2012/0089063 A1 4/2012 Olson et al.
2012/0256381 A1 10/2012 Bradshaw
2012/0289870 A1 11/2012 Hsiao-Wecksler et al.
2013/0090580 A1 4/2013 Hong et al.
2013/0102934 A1 4/2013 Ikeuchi
2013/0226048 A1 8/2013 Unluhisarcikli et al.
2013/0231595 A1 9/2013 Zoss et al.
2014/0100494 A1 4/2014 Sarkodie-Gyan et al.
2014/0330431 A1 11/2014 Hollander et al.
2015/0141878 A1 5/2015 Roy et al.
2015/0164731 A1 6/2015 Kwak et al.
2015/0173993 A1 6/2015 Walsh et al.
2015/0196403 A1 7/2015 Kim et al.
2015/0257902 A1 9/2015 Martin
2016/0030201 A1 2/2016 Zoss et al.
2016/0107309 A1 4/2016 Walsh et al.
2016/0143800 A1 5/2016 Hyung et al.
2016/0278948 A1 9/2016 Piercy et al.
2016/0331557 A1 11/2016 Tong et al.
2016/0331624 A1 11/2016 Sankai et al.
2017/0043476 A1 2/2017 Seo et al.
2017/0043482 A1 2/2017 Hyun et al.
2017/0119132 A1 5/2017 Pruess et al.
2017/0202724 A1 7/2017 De Rossi et al.
2017/0354529 A1 12/2017 Han et al.
2018/0104075 A1 4/2018 Mooney et al.
2018/0116826 A1 5/2018 Byars et al.
2018/0125738 A1 5/2018 Witte et al.
2018/0177665 A1 6/2018 Rogozinski
2018/0193172 A1 7/2018 Smith et al.
2018/0200135 A1 7/2018 Tung et al.
2018/0325764 A1 11/2018 Yagi
2019/0011743 A1 1/2019 Yan et al.
2019/0038448 A1 2/2019 Choi et al.
2019/0065970 A1 2/2019 Bonutti et al.
2019/0070060 A1 3/2019 Choi et al.
2019/0083002 A1 3/2019 Jang et al.
2019/0105215 A1 4/2019 Dalley et al.
2019/0105777 A1 4/2019 Dalley et al.

(56) References Cited

U.S. PATENT DOCUMENTS

| | | | |
|---|---|---|---|
| 2019/0125004 | A1 | 5/2019 | Thomas et al. |
| 2019/0159728 | A1 | 5/2019 | Pritchard et al. |
| 2019/0159954 | A1 | 5/2019 | Ozsecen et al. |
| 2019/0160321 | A1 | 5/2019 | Ozsecen et al. |
| 2019/0175365 | A1 | 6/2019 | Herr et al. |
| 2019/0183713 | A1 | 6/2019 | Sankai |
| 2019/0254908 | A1 | 8/2019 | Ortlieb et al. |
| 2019/0254909 | A1 | 8/2019 | Lee et al. |
| 2019/0282429 | A1 | 9/2019 | Son et al. |
| 2019/0314185 | A1 | 10/2019 | Yuge et al. |
| 2019/0328552 | A1 | 10/2019 | Herr et al. |
| 2019/0328604 | A1 | 10/2019 | Contreras-Vidal et al. |
| 2019/0343707 | A1 | 11/2019 | Riener et al. |
| 2019/0343710 | A1 | 11/2019 | Lerner |
| 2019/0344433 | A1 | 11/2019 | Lerner |
| 2019/0365554 | A1 | 12/2019 | Davies-Sekle |
| 2020/0011406 | A1 | 1/2020 | Julin |
| 2020/0016020 | A1 | 1/2020 | Mooney et al. |
| 2020/0018589 | A1 | 1/2020 | Ausserlechner |
| 2020/0085666 | A1 | 3/2020 | Seo et al. |
| 2020/0093679 | A1 | 3/2020 | Sonar et al. |
| 2020/0160020 | A1 | 5/2020 | Cho et al. |
| 2020/0188214 | A1 | 6/2020 | Lee et al. |
| 2020/0188215 | A1 | 6/2020 | Park et al. |
| 2020/0197253 | A1 | 6/2020 | Park et al. |
| 2020/0253772 | A1 | 8/2020 | Reid et al. |
| 2020/0253774 | A1 | 8/2020 | Pismennaya et al. |
| 2020/0276698 | A1 | 9/2020 | Ding et al. |
| 2020/0326780 | A1 | 10/2020 | Kearney et al. |
| 2021/0085554 | A1 | 3/2021 | Roh et al. |
| 2021/0121355 | A1 | 4/2021 | Behboodi et al. |
| 2021/0290470 | A1 | 9/2021 | Farris et al. |
| 2021/0291355 | A1 | 9/2021 | Lerner et al. |
| 2021/0298984 | A1* | 9/2021 | Bulea ........................ A61H 3/00 |
| 2021/0369536 | A1* | 12/2021 | Mooney ................. G16H 20/30 |
| 2021/0369537 | A1* | 12/2021 | Witte ................... A61B 5/1038 |
| 2021/0370495 | A1* | 12/2021 | Swartz ................... B25J 9/0006 |
| 2021/0393467 | A1 | 12/2021 | Ookoba |
| 2022/0031552 | A1 | 2/2022 | Mooney et al. |
| 2022/0079792 | A1* | 3/2022 | Lear .......................... A61F 2/70 |
| 2022/0110814 | A1 | 4/2022 | Mooney et al. |
| 2022/0273469 | A1 | 9/2022 | Kazerooni et al. |

FOREIGN PATENT DOCUMENTS

| | | | |
|---|---|---|---|
| CN | 105213155 | A | 1/2016 |
| CN | 103813772 | B | 7/2016 |
| CN | 104644381 | B | 8/2016 |
| CN | 104983543 | B | 8/2016 |
| CN | 107115191 | A | 9/2017 |
| CN | 107874984 | A | 4/2018 |
| CN | 105213153 | B | 6/2018 |
| CN | 105963100 | B | 7/2018 |
| CN | 108283564 | A | 7/2018 |
| CN | 108338896 | A | 7/2018 |
| CN | 108451748 | A | 8/2018 |
| CN | 106491319 | B | 12/2018 |
| CN | 105456004 | B | 2/2019 |
| CN | 109646245 | A | 4/2019 |
| CN | 209107991 | U | 7/2019 |
| CN | 209270231 | | 8/2019 |
| CN | 110327189 | A | 10/2019 |
| CN | 110478191 | A | 11/2019 |
| CN | 110575350 | A | 12/2019 |
| EP | 2 621 413 | B1 | 6/2014 |
| EP | 2 564 817 | B1 | 1/2019 |
| IN | 201631013395 | A | 10/2017 |
| JP | 5935177 | B2 | 6/2016 |
| KR | 101104065 | B1 | 1/2012 |
| KR | 20140107029 | A | 9/2014 |
| WO | WO-2016/180073 | A1 | 11/2016 |
| WO | WO-2016/182473 | A1 | 11/2016 |
| WO | WO-2018/023109 | A1 | 2/2018 |
| WO | WO-2019/060791 | A1 | 3/2019 |
| WO | WO-2019/160532 | A1 | 8/2019 |

OTHER PUBLICATIONS

Weerasingha et al., C-JAE: 3 DOF Robotic Ankle Exoskeleton with Compatible Joint Axes, 2018, IEEE, p. 270-275 (Year: 2018).*

Dollar et al., Active Orthoses for the Lower-Limbs: Challenges and State of the Art, 2007, IEEE, p. 968-977 (Year: 2007).*

Dollar et al., Lower Extremity Exoskeletons and Active Orthoses: Challenges and State-of-the-Art, 2008, IEEE, p. 144-158 (Year: 2008).*

European Extended Search Report issued in corresponding European Patent Application No. 21817832.5 dated May 29, 2024 (10 pages).

European Extended Search Report issued in corresponding European Patent Application No. 21818627.8 dated May 15, 2024.

Final Office Action on U.S. Appl. No. 17/002,556 Dtd Feb. 1, 2024.

Notice of Allowance on U.S. Appl. No. 17/002,556 Dtd May 15, 2024.

Partial Supplementary European Search Report issued in corresponding European Patent Application No. 21817291.4 dated May 23, 2024 (11 pages).

US Non-Final Office Action on U.S. Appl. No. 18/238,612 dated Jun. 3, 2024.

Dollar et al., "Active Orthoses for the Lower-Limbs: Challenges and State of the Art," IEEE, Jan. 14, 2008, pp. 968-977.

Dollar et al., "Lower Extremity Exoskeletons and Active Orthoses: Challenges and State-of-the-Art," IEEE, Feb. 25, 2008, pp. 144-158.

EP Office Action on EP Appl. Ser. No. 20888375.1 dated Sep. 14, 2023 (7 pages).

Goldfarb et al., "Design of a Controlled-Brake Orthosis for FES-aided Gait," IEEE, vol. 4, No. 1, Mar. 1996, pp. 13-24.

Haque et al., "Design and Preliminary Testing of an Instrumented Exoskeleton for Walking Gait Measurement," IEEE, Apr. 12, 2019, 6 pages.

International Preliminary Report on Patentability on PCT Appl. Ser. No. PCT/US2020/059866 dated May 27, 2022 (14 pages).

International Preliminary Report on Patentability on PCT Appl. Ser. No. PCT/US2021/034086 dated Dec. 15, 2022 (10 pages).

International Preliminary Report on Patentability on PCT Appl. Ser. No. PCT/US2021/034163 dated Dec. 15, 2022 (6 pages).

International Preliminary Report on Patentability on PCT Appl. Ser. No. PCT/US2021/034182 dated Dec. 15, 2022 (5 pages).

International Preliminary Report on Patentability on PCT Appl. Ser. No. PCT/US2021/034252 dated Dec. 15, 2022 (14 pages).

International Preliminary Report on Patentability on PCT Appl. Ser. No. PCT/US2021/047252 dated Mar. 9, 2023 (9 pages).

International Preliminary Report on Patentability on PCT Appl. Ser. No. PCT/US2021/047295 dated Mar. 30, 2023 (5 pages).

International Search Report and the Written Opinion on PCT Appl. Ser. No. PCT/US2020/059866 dated Feb. 4, 2021 (8 pages).

International Search Report and the Written Opinion on PCT Appl. Ser. No. PCT/US2021/034086 dated Jun. 28, 2021 (11 pages).

International Search Report and the Written Opinion on PCT Appl. Ser. No. PCT/US2021/034163 dated Jun. 25, 2021 (7 pages).

International Search Report and the Written Opinion on PCT Appl. Ser. No. PCT/US2021/034182 dated Jun. 29, 2021 (6 pages).

International Search Report and the Written Opinion on PCT Appl. Ser. No. PCT/US2021/034252 dated Jun. 28, 2021 (15 pages).

International Search Report and the Written Opinion on PCT Appl. Ser. No. PCT/US2021/047252 dated Nov. 23, 2021 (10 pages).

International Search Report and the Written Opinion on PCT Appl. Ser. No. PCT/US2021/047295 dated Sep. 23, 2021 (7 pages).

Kim et al., "Mechanical Design of the Hanyang Exoskeleton Assistive Robot (HEXAR)," Dec. 18, 2014, IEEE, pp. 479-484.

Pirjade et al., "Design and Fabrication of a Low-cost Human Body Lower Limb Exoskeleton," IEEE, Apr. 16, 2020, pp. 32-37.

Sanz-Morere et al., "A Knee-Ankle-Foot Orthosis to Assist the Sound Limb of Transfemoral Amputees," IEEE, vol. 1, No. 1, Feb. 13, 2019, pp. 38-48.

US Corrected Notice of Allowance on U.S. Appl. No. 17/504,261 dated Apr. 24, 2023 (2 pages).

US Corrected Notice of Allowance on U.S. Appl. No. 17/504,261 dated May 18, 2023 (2 pages).

(56) References Cited

OTHER PUBLICATIONS

US Final Office Action on U.S. Appl. No. 17/028,761 dated Mar. 16, 2021 (18 pages).
US Final Office Action on U.S. Appl. No. 17/136,333 dated Jun. 21, 2021 (27 pages).
US Final Office Action on U.S. Appl. No. 17/526,454 dated Apr. 7, 2023 (6 pages).
US Non-Final Office Action on U.S. Appl. No. 17/002,556 dated Aug. 21, 2023 (107 pages).
US Non-Final Office Action on U.S. Appl. No. 17/022,982 dated May 4, 2021 (19 pages).
US Non-Final Office Action on U.S. Appl. No. 17/028,761 dated Nov. 23, 2020 (18 pages).
US Non-Final Office Action on U.S. Appl. No. 17/028,761 dated Oct. 12, 2021 (24 pages).
US Non-Final Office Action on U.S. Appl. No. 17/136,333 dated Mar. 12, 2021 (24 pages).
US Non-Final Office Action on U.S. Appl. No. 17/136,333 dated Nov. 23, 2021 (28 pages).
US Non-Final Office Action on U.S. Appl. No. 17/504,248 dated Jun. 7, 2023 (12 pages).
US Non-Final Office Action on U.S. Appl. No. 17/504,261 dated Dec. 20, 2022 (9 pages).
US Non-Final Office Action on U.S. Appl. No. 17/526,454 dated Jan. 12, 2023 (22 pages).
US Non-Final Office Action on U.S. Appl. No. 17/867,162 dated Apr. 12, 2023 (32 pages).
US Notice of Allowance on U.S. Appl. No. 17/022,982 dated Jan. 29, 2021 (12 pages).
US Notice of Allowance on U.S. Appl. No. 17/022,982 dated Sep. 27, 2021 (9 pages).
US Notice of Allowance on U.S. Appl. No. 17/028,761 dated Feb. 2, 2022 (10 pages).
US Notice of Allowance on U.S. Appl. No. 17/084,111 dated Feb. 19, 2021 (13 pages).
US Notice of Allowance on U.S. Appl. No. 17/084,111 dated May 20, 2021 (8 pages).
US Notice of Allowance on U.S. Appl. No. 17/084,111 dated Sep. 16, 2021 (7 pages).
US Notice of Allowance on U.S. Appl. No. 17/109,911 dated Feb. 3, 2021 (10 pages).
US Notice of Allowance on U.S. Appl. No. 17/109,911 dated May 25, 2021 (5 pages).
US Notice of Allowance on U.S. Appl. No. 17/109,911 dated Sep. 14, 2021 (5 pages).
US Notice of Allowance on U.S. Appl. No. 17/136,333 dated Apr. 6, 2022 (13 pages).
US Notice of Allowance on U.S. Appl. No. 17/504,248 dated Nov. 28, 2023 (9 pages).
US Notice of Allowance on U.S. Appl. No. 17/504,261 dated Apr. 7, 2023 (9 pages).
US Notice of Allowance on U.S. Appl. No. 17/526,454 dated Apr. 26, 2023 (8 pages).
US Notice of Allowance on U.S. Appl. No. 17/867,162 dated Aug. 30, 2023 (17 pages).
US Notice of Allowance on U.S. Appl. No. 17/867,162 dated Oct. 30, 2023 (18 pages).
US Notice of Allowance on U.S. Appl. No. 17/867,162 dated Oct. 5, 2023 (18 pages).
Witte et al., "Design of Two Lightweight, High-Bandwidth Torque-Controlled Ankle Exoskeletons," IEEE International Conference on Robotics and Automation (ICRA), May 26, 2015 (6 pages).
Xie et al., "An Unpowered Flexible Lower Limb Exoskeleton: Walking Assisting and Energy Harvesting," IEEE, vol. 24, No. 5, Oct. 5, 2019, pp. 2236-2247.
Zhang et al., "Experimental comparison of torque control methods on an ankle exoskeleton during human walking," IEEE International Conference on Robotics and Automation (ICRA), May 26, 2015 (6 pages).
Zhou et al., "Preliminary Evaluation of Gait Assistance During Treadmill Walking with a Light-weight Bionic Knee Exoskeleton," IEEE, Dec. 7, 2016, pp. 1173-1178.
US Non-Final Office Action on U.S. Appl. No. 17/717,347 dated Sep. 19, 2024 (23 pages).
European Extended Search Report issued in corresponding European Patent Application No. 21817826.7 dated Jun. 14, 2024 (6 pages).
Office Action issued in corresponding European Patent Application No. 21817291.4 dated Aug. 13, 2024 (10 pages).
Office Action issued in corresponding European Patent Application No. 21862525.9 dated Aug. 26, 2024 (5 pages).
Office Action issued in corresponding European Patent Application No. 21869964.3 dated Aug. 13, 2024 (5 pages).
US Notice of Allowance on U.S. Appl. No. 18/238,612 dated Sep. 11, 2024.
US Non-Final Office Action on U.S. Appl. No. 18/594,930 dated Nov. 7, 2024 (78 pages).
Office Action issued in corresponding European Patent Application No. 20888375.1 dated Apr. 17, 2025.
US Notice of Allowance on U.S. Appl. No. 18/594,930 dated Apr. 30, 2025.
US Non-Final Office Action on U.S. Appl. No. 17/717,347 dated Jan. 28, 2025.
US Non-Final Office Action on U.S. Appl. No. 17/776,144 dated May 19, 2025.

* cited by examiner

SYSTEMS AND METHODS FOR AN ACTIVE EXOSKELETON WITH LOCAL BATTERY

CROSS-REFERENCES TO RELATED APPLICATIONS

This application claims the benefit of priority under 35 U.S.C. § 120 as a continuation of U.S. patent application Ser. No. 17/526,454, filed Nov. 15, 2021, which claims the benefit of priority under 35 U.S.C. § 120 as a continuation of U.S. patent application Ser. No. 17/022,982, filed Sep. 16, 2020, each of which is hereby incorporated herein by reference in its entirety.

GOVERNMENT RIGHTS

This invention was made with government support under contract no. W911QY-19-9-0007 awarded by Natick Contracting Division. This Agreement is not subject to the Bayh-Dole Act, 35 U.S.C. §§ 200-212.

TECHNICAL FIELD

The present disclosure generally relates to the field of exoskeletons.

BACKGROUND

Exoskeletons can be worn by a user to facilitate movement of limbs of the user.

SUMMARY

At least one aspect of the present disclosure is directed to an apparatus for a battery-powered active exoskeleton boot. The apparatus can include a shin pad to be coupled to a shin of a user below a knee of the user. The apparatus can include one or more housings enclosing electronic circuitry and an electric motor that can generate torque about an axis of rotation of an ankle joint of the user. At least one of the one or more housings can be coupled to the shin pad below the knee of the user. The apparatus can include a battery holder coupled to the shin pad. The battery holder can be located below the knee of the user and above the one or more housings enclosing the electronic circuitry. The apparatus can include a battery module held in the battery holder. The battery module can include a first power connector that electrically couples to a second power connector located in the battery holder to provide electric power to the electronic circuitry and the electric motor. The apparatus can include an output shaft coupled to the electric motor and extending through a bore in a housing of the one or more housings enclosing the electric motor. The electronic circuitry can control delivery of power from the battery module to the electric motor to generate torque about the axis of rotation of the ankle joint of the user.

Another aspect of the present disclosure is directed to a system for a battery-powered active exoskeleton boot. The system can include a shin pad of an exoskeleton to be coupled to a shin of a user below a knee of the user. The system can include one or more housings enclosing electronic circuitry and an electric motor that can generate torque about an axis of rotation of an ankle joint of the user. At least one of the one or more housings can be coupled to the shin pad below the knee of the user. The system can include a battery module held by the exoskeleton below the knee of the user and above the one or more housing enclosing the electronic circuitry. The battery module can include a first power connector that electrically couples to a second power connector to provide electric power to the electronic circuitry and the electric motor. The system can include one or more processors. The one or more processors can receive data corresponding to a performance of the battery module. The data can include one or more of a temperature, current, voltage, battery percentage. The one or more processors can determine, based on a safety policy, to trigger a safety action. The one or more processors can instruct, based on the safety action, the electronic circuitry to adjust an amount of power delivered from the battery module to the electric motor to adjust an amount of torque generated about the axis of rotation of the ankle joint of the user.

Another aspect of the present disclosure is directed to a method of augmenting user motion. The method can include providing a battery-powered active exoskeleton boot. The battery-powered active exoskeleton boot can include a shin pad to be coupled to a shin of a user below a knee of the user. The battery-powered active exoskeleton boot can include one or more housings enclosing electronic circuitry and an electric motor that can generate torque about an axis of rotation of an ankle joint of the user. At least one of the one or more housings can be coupled to the shin pad below the knee of the user. The battery-powered active exoskeleton boot can include a battery holder coupled to the shin pad. The battery holder can be located below the knee of the user and above the one or more housings enclosing the electronic circuitry. The battery-powered active exoskeleton boot can include a battery module held in the battery holder. The battery module can include a first power connector that electrically couples to a second power connector located in the battery holder while attached to the battery holder to provide electric power to the electronic circuitry and the electric motor. The battery-powered active exoskeleton boot can include an output shaft coupled to the electric motor and extending through a bore in a housing of the one or more housings enclosing the electric motor. The electronic circuitry can control delivery of power from the battery module to the electric motor to generate torque about the axis of rotation of the ankle joint of the user.

Those skilled in the art will appreciate that the summary is illustrative only and is not intended to be in any way limiting. Other aspects, inventive features, and advantages of the devices and/or processes described herein, as defined solely by the claims, will become apparent in the detailed description set forth herein and taken in conjunction with the accompanying drawings.

BRIEF DESCRIPTION OF THE DRAWINGS

The details of one or more implementations of the subject matter described in this specification are set forth in the accompanying drawings and the description below. Other features, aspects, and advantages of the subject matter will become apparent from the description, the drawings, and the claims.

Like reference numbers and designations in the various drawings indicate like elements.

DETAILED DESCRIPTION

This disclosure relates generally to performance enhancing wearable technologies. Particularly, this disclosure relates to apparatuses, systems, and methods for an active exoskeleton with a local battery. The local battery can include an onboard power source that is used to power electronics and one or more actuators.

I. Exoskeleton Overview

Exoskeletons (e.g., battery-powered active exoskeleton, battery-powered active exoskeleton boot, lower limb exoskeleton, knee exoskeleton, or back exoskeleton) can include devices worn by a person to augment physical abilities. Exoskeletons can be considered passive (e.g., not requiring an energy source such as a battery) or active (e.g., requiring an energy source to power electronics and usually one or many actuators). Exoskeletons may be capable of providing large amounts of force, torque and/or power to the human body in order to assist with motion.

Exoskeletons can transfer energy to the user or human. Exoskeletons may not interfere with the natural range of motion of the body. For example, exoskeletons can allow a user to perform actions (e.g., walking, running, reaching, or jumping) without hindering or increasing the difficulty of performing these actions. Exoskeletons can reduce the difficulty of performing these actions by reducing the energy or effort the user would otherwise exert to perform these actions. Exoskeletons can convert the energy into useful mechanical force, torque, or power. Onboard electronics (e.g., controllers) can control the exoskeleton. Output force and torque sensors can also be used to make controlling easier.

Figure 1:
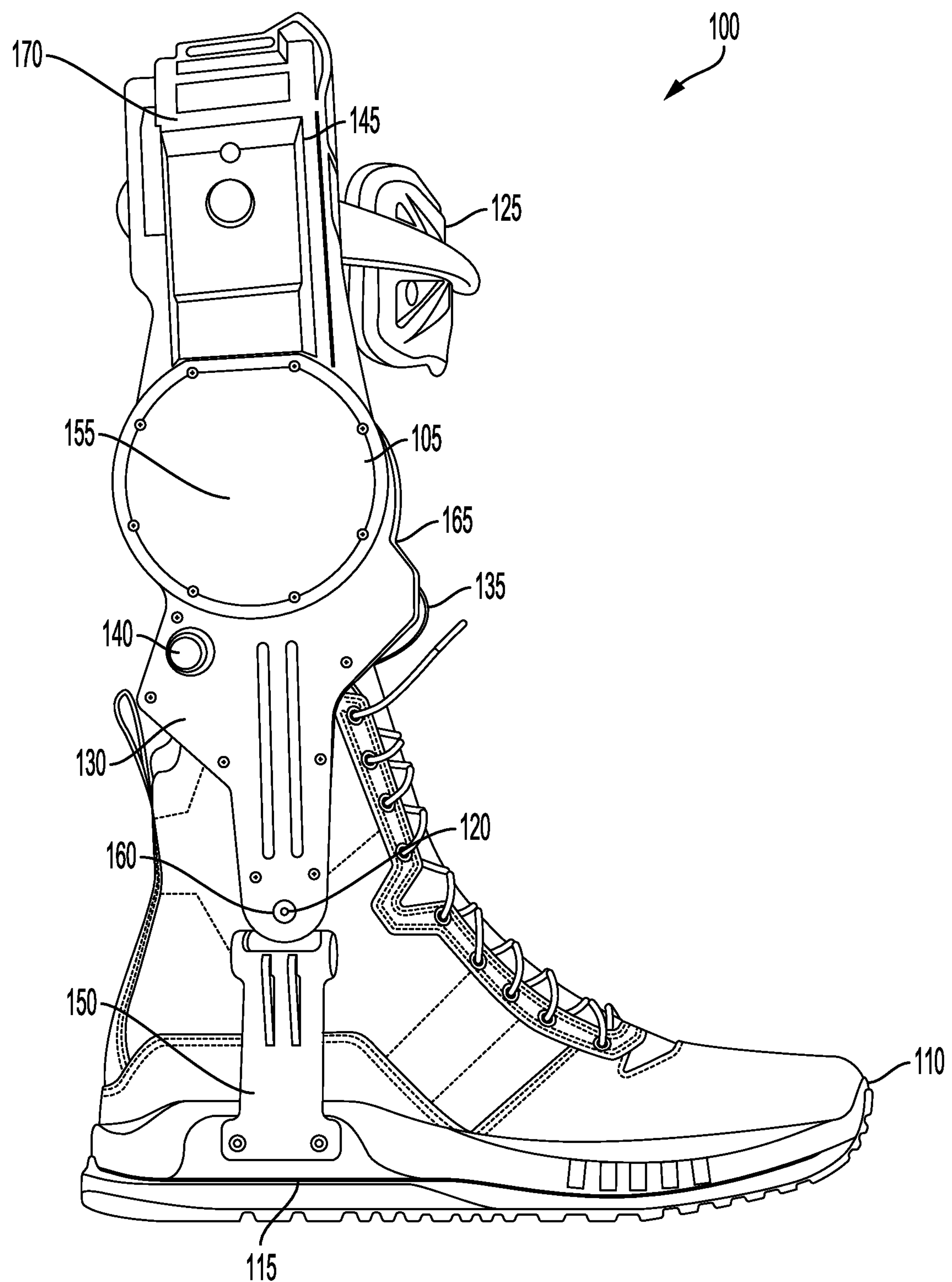
FIG. 1 illustrates a schematic diagram of an exoskeleton, according to an embodiment.

FIG. 1 illustrates a schematic diagram of an exoskeleton 100. The exoskeleton 100 can be referred to as a lower limb exoskeleton, lower limb exoskeleton assembly, lower limb exoskeleton system, ankle exoskeleton, ankle foot orthosis, knee exoskeleton, hip exoskeleton, exoskeleton boot, or exoboot. The exoskeleton 100 can include a water resistant active exoskeleton boot. For example, the exoskeleton 100 can resist the penetration of water into the interior of the exoskeleton 100. The exoskeleton 100 can include a water resistant active exoskeleton boot. For example, the exoskeleton 100 can be impervious to liquids (e.g., water) and non-liquids (e.g., dust, dirt, mud, sand, or debris). The exoskeleton 100 can remain unaffected by water or resist the ingress of water, such as by decreasing a rate of water flow into the interior of the exoskeleton 100 to be less than a target rate indicative of being water resistant or waterproof. For example, the exoskeleton 100 can operate in 3 feet of water for a duration of 60 minutes. The exoskeleton 100 can have an ingress protection rating (IP) rating of 68. The exoskeleton 100 can have a National Electrical Manufacturer Association (NEMA) rating of 4×, which can indicate that the exoskeleton 100 has a degree of protection with respect to harmful effects on the equipment due to the ingress of water (e.g., rain, sleet, snow, splashing water, and hose directed water), and that the exoskeleton can be undamaged by the external formation of ice on the enclosure.

The exoskeleton 100 can include a shin pad 125 (e.g., shin guard). The shin pad 125 can be coupled to a shin of a user below a knee of the user. The shin pad 125 can be coupled to the shin of the user to provide support. The shin pad 125 can include a piece of equipment to protect the user from injury. For example, the shin pad 125 can protect the lower extremities of the user from external impact. The shin pad 125 can interface with the shin of the user. The shin pad 125 can include a band (e.g., adjustable band) configured to wrap around the shin of the user. The shin pad 125 can secure the upper portion of the exoskeleton 100 to the body of the user. The shin pad 125 can secure or help secure the exoskeleton 100 to the shin, leg, or lower limb of the user. The shin pad 125 can provide structural integrity to the exoskeleton 100. The shin pad 125 can support other components of the exoskeleton 100 that can be coupled to the shin pad 125. The shin pad 125 can be made of lightweight, sturdy, and/or water resistant materials. For example, the shin pad 125 can be made of plastics, aluminum, fiberglass, foam rubber, polyurethane, and/or carbon fiber.

The exoskeleton 100 can include one or more housings 105. At least one of the one or more housings 105 can be coupled to the shin pad 125 below the knee of the user. The shin pad 125 can be coupled to the at least one housing via a shin lever. The shin lever can extend from the at least one housing to the shin pad 125. The shin lever can include a mechanical structure that connects the shin pad 125 to a chassis. The chassis can include a mechanical structure that connects static components.

The one or more housings 105 can enclose electronic circuitry (e.g., electronic circuitry 1405). The one or more housings 105 can encapsulate some or all the electronics of the exoskeleton 100. The one or more housings 105 can include an electronics cover (e.g., case). The one or more housings 105 can enclose an electric motor (e.g., motor 1230). The electric motor can generate torque about an axis of rotation of an ankle joint of the user. The ankle joint can allow for dorsiflexion and/or plantarflexion of the user's foot. The exoskeleton 100 can include an ankle joint component 120 that rotates about the axis of rotation the ankle joint. The ankle joint component 120 can be positioned around or adjacent to the ankle joint.

The exoskeleton 100 can include a rotary encoder 155 (e.g., shaft encoder, first rotary encoder, or motor encoder). The rotary encoder 155 can be enclosed within the one or more housings 105. The rotary encoder 155 can measure an angle of the electric motor. The angle of the electric motor can be used by the controller to determine an amount of torque applied by the exoskeleton 100. For example, the angle of the electric motor can correspond to an amount of torque applied by the exoskeleton 100. An absolute angle of the electric motor can correspond to an amount of torque applied by the exoskeleton 100. The rotary encoder 155 can include an inductive encoder. The ankle joint component 120 can be actuated by a motor (e.g., electric motor). The rotary encoder 155 can include a contactless magnetic encoder or an optical encoder.

The exoskeleton 100 can include a second rotary encoder 160 (e.g., ankle encoder). The second rotary encoder 160 can measure an angle of the ankle joint. The angle of the ankle joint can be used by the controller to determine an amount of torque applied by the exoskeleton 100. The second rotary encoder 160 can include a first component enclosed in the one or more housings 105 and in communication with the electronic circuitry 1405. The second rotary encoder 160 can include a second component located outside the one or more housings 105 and configured to interact with the first component. The second rotary encoder 160 can include a contactless magnetic encoder, a contactless inductive encoder, or an optical encoder. The second rotary encoder 160 can detect the angle of the ankle joint while the rotary encoder 155 can detect the angle of the electric motor. The angle of the electric motor can be different from the angle of the ankle joint. The angle of the electric motor can be independent of the angle of the ankle joint. The angle of the ankle joint can be used to determine an output (e.g., torque) of the electric motor. The ankle joint component 120 can be coupled to the second rotary encoder 160.

The one or more housings 105 can encapsulate electronics that are part of the exoskeleton 100. The one or more housings 105 can form a fitted structure (e.g., clamshell structure) to enclose the electronic circuitry and the electric motor. The fitted structure can be formed from two or more individual components. The individual components of the fitted structure can be joined together to form a single unit. The one or more housings 105 can be formed of plastic or metal (e.g., aluminum). An adhesive sealant can be placed between individual components of the fitted structure and under the electronics cover. A gasket can be placed between individual components of the fitted structure and under the electronics cover. The gasket can be placed in the seam between the individual components of the fitted structure.

A sealant 165 can be placed in contact with the one or more housings 105 to close the one or more housings 105 and prevent an ingress of water into the one or more housings 105. The sealant 165 used to close the one or more housings 105 can include an adhesive sealant (e.g., super glue, epoxy resin, or polyvinyl acetate). The adhesive sealant can include a substance used to block the passage of fluids through the surface or joints of the one or more housings 105. The sealant 165 used to close the one or more housings 105 can include epoxy. The sealant 165 can permanently seal or close the one or more housings 105. For example, the sealant 165 can seal or close the one or more housings 105 such that the one or more housings are not removably attached to one another.

The exoskeleton 100 can couple with a boot 110. For example, the exoskeleton 100 can be attached to the boot 110. The boot 110 can be worn by the user. The boot 110 can be connected to the exoskeleton 100. The exoskeleton 100 can be compatible with different boot shapes and sizes.

The exoskeleton 100 can include an actuator 130 (e.g., actuator lever arm, or actuator module). The actuator 130 can include one or more of the components in the exoskeleton 100. For example, the actuator 130 can include the one or more housings 105, the footplate 115, the ankle joint component 120, the actuator belt 135, and the post 150, while excluding the boot 110. The boot 110 can couple the user to the actuator 130. The actuator 130 can provide torque to the ground and the user.

The exoskeleton 100 can include a footplate 115 (e.g., carbon insert, carbon shank). The footplate 115 can include a carbon fiber structure located inside of the sole of the boot 110. The footplate 115 can be made of a carbon-fiber composite. The footplate 115 can be inserted into the sole of the boot 110. The footplate 115 can be used to transmit torque from the actuator 130 to the ground and to the user. The footplate 115 can be located in the sole of the exoskeleton 100. This footplate 115 can have attachment points that allow for the connection of the exoskeleton's mechanical structure. An aluminum insert with tapped holes and cylindrical bosses can be bonded into the footplate 115. This can create a rigid mechanical connection to the largely compliant boot structure. The bosses provide a structure that can be used for alignment. The footplate 115 can be sandwiched between two structures, thereby reducing the stress concentration on the part. This design can allow the boot to function as a normal boot when there is no actuator 130 attached.

The exoskeleton 100 can include an actuator belt 135 (e.g., belt drivetrain). The actuator belt 135 can include a shaft that is driven by the motor and winds the actuator belt 135 around itself. The actuator belt 135 can include a tensile member that is pulled by the spool shaft and applies a force to the ankle lever. Tension in the actuator belt 135 can apply a force to the ankle lever. The exoskeleton 100 can include an ankle lever. The ankle lever can include a lever used to transmit torque to the ankle. The exoskeleton 100 can be used to augment the ankle joint.

The exoskeleton 100 can include a power button 140 (e.g., switch, power switch). The power button 140 can power the electronics of the exoskeleton 100. The power button 140 can be located on the exterior of the exoskeleton 100. The power button 140 can be coupled to the electronics in the interior of the exoskeleton 100. The power button 140 can be electrically connected to an electronic circuit. The power button 140 can include a switch configured to open or close the electronic circuit. The power button 140 can include a low-power, momentary push-button configured to send power to a microcontroller. The microcontroller can control an electronic switch.

The exoskeleton 100 can include a battery holder 170 (e.g., charging station, dock). The battery holder 170 can be coupled to the shin pad 125. The battery holder 170 can be located below the knee of the user. The battery holder 170 can be located above the one or more housings 105 enclosing the electronic circuitry. The exoskeleton 100 can include a battery module 145 (e.g., battery). The battery holder 170 can include a cavity configured to receive the battery module 145. A coefficient of friction between the battery module 145 and the battery holder 170 can be established such that the battery module 145 is affixed to the battery holder 170 due to a force of friction (e.g., frictional force) based on the coefficient of friction and a force of gravity. The coefficient of friction can include values in a range of 0.5 and 1. For example, the coefficient of friction between the battery module 145 and the battery holder 170 can include 0.5, 0.6, 0.7, 0.8, 0.9, or 1, inclusive. The frictional force can include values in a range of 1 newtons (N) and 10 newtons. For example, the frictional force can include 1 N, 2 N, 3 N, 4 N, 5 N, 6 N, 7 N, 8 N, 9 N, or 10 N, inclusive. The battery module 145 can be affixed to the battery holder 170 absent a mechanical button or mechanical latch. The battery module 145 can be affixed to the battery holder 170 via a lock, screw, or toggle clamp. The battery holder 170 and the battery module 145 can be an integrated component (e.g., integrated battery). The integrated battery can be supported by a frame of the exoskeleton 100 as opposed to having a separated enclosure. The integrated battery can include a charging port. For example, the charging port can include a barrel connector or a bullet connector. The integrated battery can include cylindrical cells or prismatic cells.

The battery module 145 can power the exoskeleton 100. The battery module 145 can include one or more electrochemical cells. The battery module 145 can supply electric power to the exoskeleton 100. The battery module 145 can include a power source (e.g., onboard power source). The power source can be used to power electronics and one or more actuators. The battery module 145 can include a battery pack. The battery pack can be coupled to the one or more housings 105 below a knee of the user. The battery pack can include an integrated battery pack. The integrated battery pack can remove the need for power cables, which can reduce the snag hazards of the system. The integrated battery pack can allow the system to be a standalone unit mounted to the user's lower limb. The battery module 145 can include a battery management system 1224 to perform various operations. For example, the system can optimize the energy density of the unit, optimize the longevity of the cells, and enforce safety protocols to protect the user.

The battery module 145 can include a removable battery. The battery module 145 can be referred to as a local battery because it is located on the exoboot 100 (e.g., on the lower limb or below the knee of the user), as opposed to located on a waist or back of the user. The battery module 145 can include a weight-mounted battery, which can refer to the battery being held in place on the exoboots 100 via gravity and friction, as opposed to a latching mechanism. The battery module 145 can include a water resistant battery or a waterproof battery. The exoskeleton 100 and the battery module 145 can include water resistant connectors. The weight of the battery module 145 can include values in a range of 250 grams to 280 grams. For example, the weight of the battery module 145 can include 250 grams, 255 grams, 260 grams, 265 grams, 270 grams, 275 grams, or 280 grams, inclusive.

The battery module 145 can include a high-side switch (e.g., positive can be interrupted). The battery module 145 can include a ground that is always connected. The battery module 145 can include light emitting diodes (LEDs). For example, the battery module 145 can include three LEDs used for a user interface. The LEDs can be visible from one lens so that the LEDs appear as one multicolor LED. The LEDs can blink in various patterns and/or colors to communicate a state of the battery module 145 (e.g., fully charged, partially charged, low battery, or error).

The exoskeleton 100 can include a post 150. The post 150 can include a mechanical structure that connects to the boot 110. The post 150 can couple the ankle joint component 120 with the footplate 115. The post 150 can be attached at a first end to the footplate 115. The post 150 can be attached at a second end to the ankle joint component 120. The post 150 can pivot about the ankle joint component 120. The post 150 can include a mechanical structure that couples the footplate 115 with the ankle joint component 120. The post 150 can include a rigid structure. The post 150 can be removably attached to the footplate 115. The post 150 can be removably attached to the ankle joint component 120. For example, the post 150 can be disconnected from the ankle joint component 120.

The exoskeleton 100 can include a rugged system used for field testing. The exoskeleton 100 can include an integrated ankle lever guard (e.g., nested lever). The exoskeleton 100 can include a mechanical shield to guard the actuator belt 135 and ankle lever transmission from the environment. The housing structure of the system can extend to outline the range of travel of the ankle lever (e.g., lever arm 2040) on the lateral and medial side.

II. Active Exoskeleton with Local Battery

Exoskeletons 100 can transform an energy source into mechanical forces that augment human physical ability. Exoskeletons 100 can have unique power requirements. For example, exoskeletons 100 can use non-constant power levels, such as cyclical power levels with periods of high power (e.g., 100 to 1000 Watts) and periods of low or negative power (e.g., 0 Watts). Peaks in power can occur once per gait cycle. Batteries configured to provide power to the exoskeleton 100 can be the source of various issues. For example, batteries located near the waist of a user can require exposed cables that extend from the battery to the lower limb exoskeleton. These cables can introduce snag hazards, make the device cumbersome, and add mass to the system. Additionally, long cables with high peak power can result in excess radio emissions and higher voltage drops during high current peaks. Thus, systems, methods and apparatus of the present technical solution provide an exoskeleton with a local battery that can perform as desired without causing snag hazards, power losses, and radio interference. Additionally, the battery can be located close to the knee such that the mass felt by the user is reduced as compared to a battery located close the foot of the user.

Figure 2:
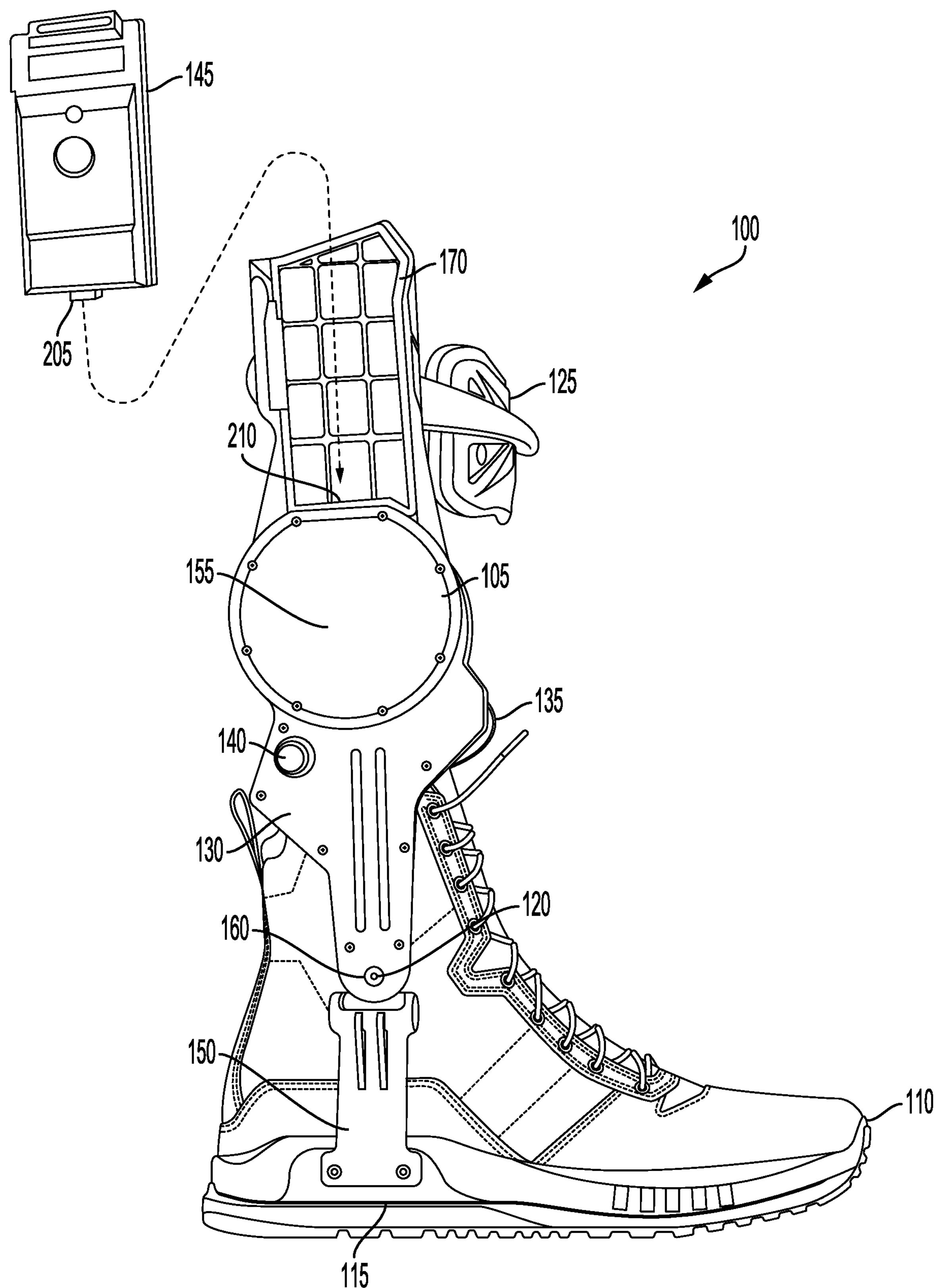
FIG. 2 illustrates a schematic diagram of an exoskeleton, according to an embodiment.

FIG. 2 illustrates a schematic diagram of the exoskeleton 100. The exoskeleton 100 includes the one or more housings 105, the boot 110 the footplate 115, the ankle joint component 120, shin pad 125, the actuator 130, the actuator belt 135, the power button 140, the battery module 145, the post 150, the rotary encoder 155, and the second rotary encoder 160. The battery module 145 can be inserted into the exoskeleton 100. The battery module 145 can include a sealed battery. The battery module 145 can coupled with the exoskeleton 100 via a waterproof or water resistant connection. The battery module 145 can connect locally (e.g., proximate) to the exoskeleton 100 such that a wire is not needed to run from the battery module 145 to the electronics.

The battery module 145 can be held in the battery holder 170. The battery module 145 can be integrated with the battery holder 170. The battery module 145 can be held by, or affixed to, the exoskeleton 100 itself. For example, the battery module 145 can be affixed, attached, or integrated with a portion of the exoskeleton 100 without a separate housing or battery holder 170.

In implementations, the battery module 145 can be held by the battery holder 170 in a fixed or integrated manner, or in a removeable manner. For example, the battery module 145 can be removably affixed to the battery holder 170. For example, the battery module 145 can slide in and out of the battery holder 170. By removably affixing the battery module 145 to the battery holder 170, the battery module 145 can be replaced with another battery module 145, or the battery module 145 can be removed for charging. The battery module 145 can include a first power connector 205 that electrically couples to a second power connector 210 located in the battery holder 170 while attached to the battery holder 170 to provide electric power to the electronic circuitry and the electric motor. The first power connector 205 and the second power connector 210 can couple (e.g., connect) the battery module 145 with the electronic circuitry. The first power connector 205 and the second power connector 210 can couple the battery module 145 with the one or more housings 105. The first power connector 205 can be recessed in the battery module 145 to protect the first power connector 205 from loading and impacts. The first power connector 205 and the second power connector 210 can include wires (e.g., two wires, three wires, or four wires). The battery module 145 can communicate with the electronic circuitry via the first power connector 205 and the second power connector 210. The first power connector 205 and the second power connector 210 can include an exposed connector.

Figure 3:
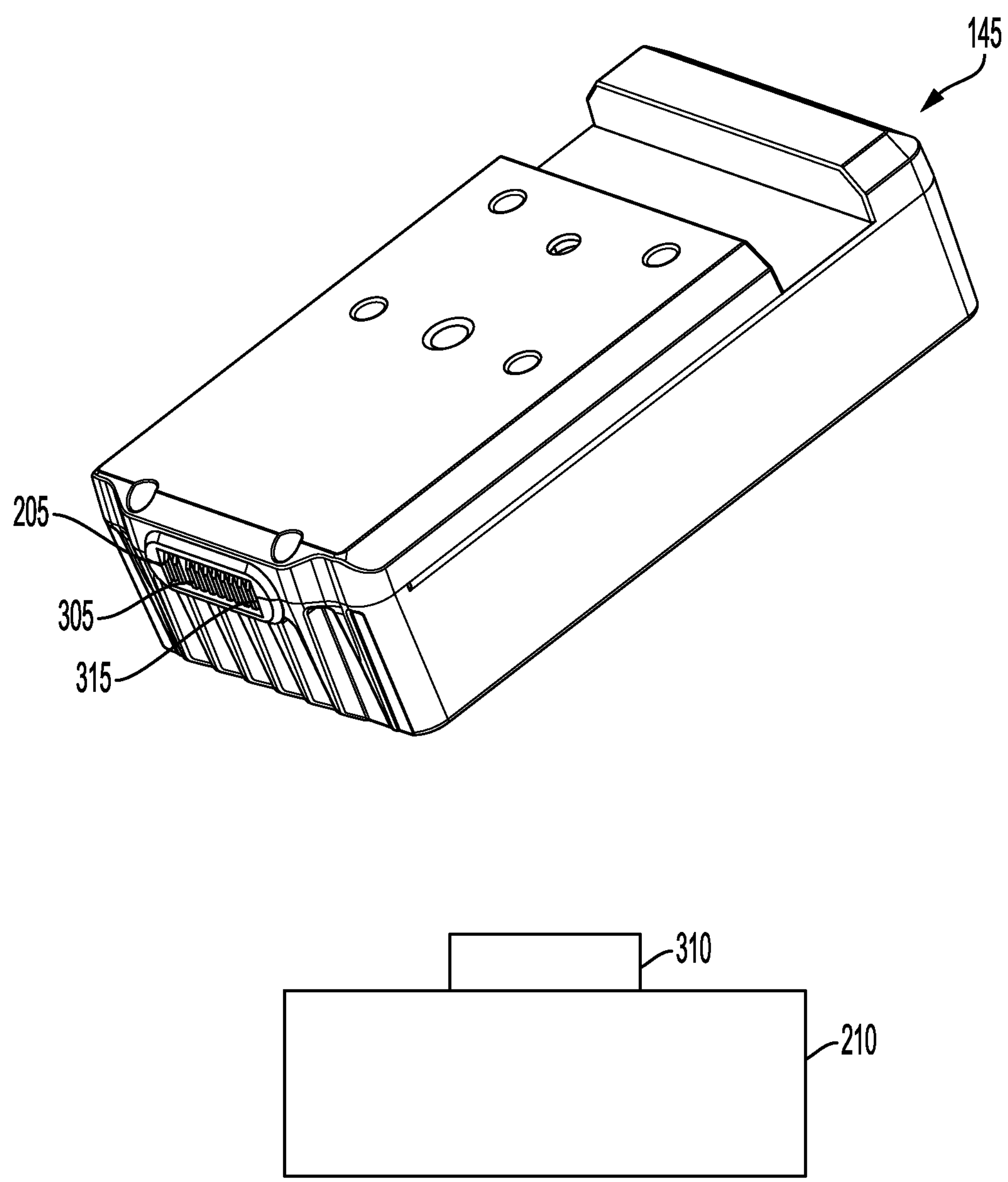
FIG. 3 illustrates a schematic diagram of a battery module, according to an embodiment.

FIG. 3 illustrates a schematic diagram of the battery module 145. The first power connector 205 can include a blade connector 305. A blade connector 305 can be a type of single wire, plug-and-socket connection using a flat conductive blade that can be inserted into a receptacle. The second power connector 210 can include a receptacle 310 configured to receive the blade connector 305 absent an exposed cable. For example, the blade connector 305 can slide into the receptacle 310. The blade connector 305 can include an asymmetric and keyed design to prevent improper affixation of the battery module 145 to the battery holder 170. The blade connector 305 can include a design to tolerate small connector misalignment. The blade connector 305 can be recessed within a power connector housing to prevent damage to the blade connector 305. The geometry of the battery module 145 can allow for storage and packing efficiency. The battery module 145 can include a gripping element to allow for ergonomic ease of removal and insertion of the battery module 145 into the battery holder 170. The battery module 145 can be made of lightweight plastics or metals. The battery module 145 can be made of heat insulating materials to prevent heat generated by the battery cells from reaching the user. One or more faces of the battery module 145 can be made of metal to dissipate heat.

The first power connector 205 can include a serial data communication port to provide at least one of battery state data, a battery test function, a smart charging function, or a firmware upgrade. The battery state data can include the health of the battery module 145. The battery test function can include probing the battery module 145. The smart charging function can include using a high voltage to charge the battery module 145. The first power connector 205 can include a pin 315. The pin 315 can provide serial data. The pin 315 can be further configured to receive a voltage input greater than or equal to a threshold to wake up a battery management system 1224 of the battery module 145. The pin 315 can be configured to receive a voltage input greater than or equal to a threshold to put the battery management system 1224 to sleep. The pin 315 can be configured to receive a voltage input greater than or equal to a threshold to put the battery management system 1224 in a bootloader mode. The pin 315 can include a serial port to allow the exoskeleton 100 to access data from the battery management system 1224. The serial port can allow a computer to be connected to the battery module 145 to monitor its state. The serial port can be used to support a bootloader (e.g., boot program, bootstrap loader). The bootloader can include a piece of software that loads into the working memory after start-up. The serial port can be used to upgrade the firmware (e.g., via the bootloader). The serial port can be connected to the power button 140. The pin 315 can wake up the battery module 145. The pin 315 can put the battery module 145 in and out of ship mode. Ship mode can include a ship mode circuit that prolongs the battery life of the battery module 145. The battery module 145 can be electronically disconnected from the rest of the system to minimize power drain while the exoskeleton 100 is idle. When the exoskeleton 100 is turned on, the battery module 145 can be connected to the rest of the exoskeleton 100 and stays connected until the system goes back into ship mode. An external signal used to put the battery in and out of ship mode. The external signal used to put the battery in an out of ship mode can used to start the bootloader.

Figure 4:
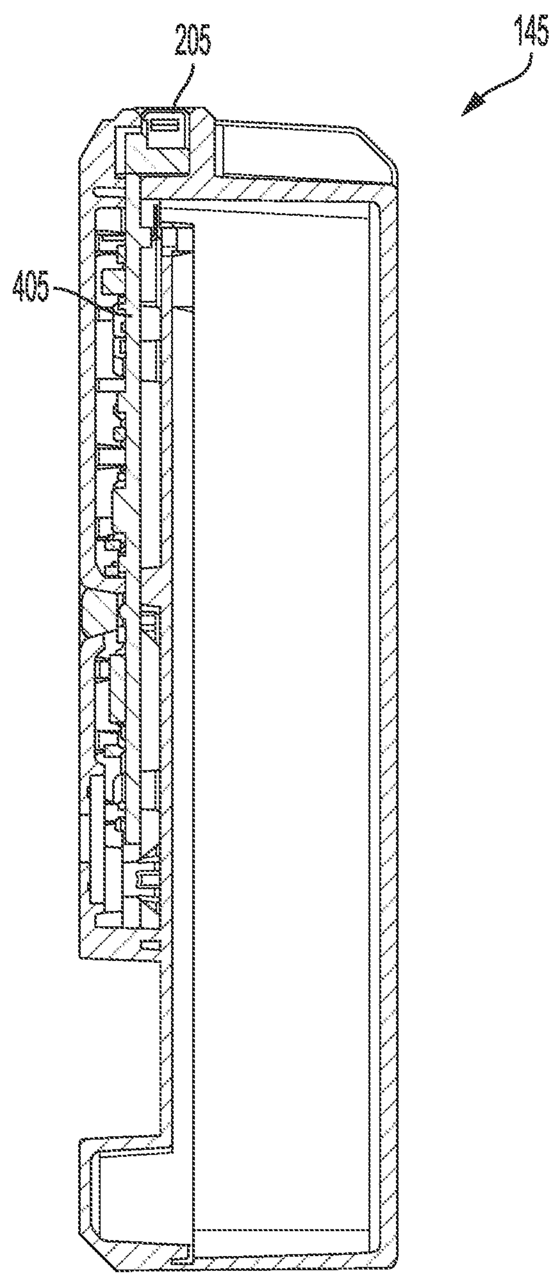
FIG. 4 illustrates a cross-section of a battery module, according to an embodiment.

FIG. 4 illustrates a cross-section of the battery module 145. The battery module 145 can include a printed circuit board 405. The printed circuit board 405 can be enclosed within the battery module 145. The battery module 145 can include the first power connector 205. The first power connector 205 can disposed on an exterior of the battery module 145. The first power connector 205 can be coupled to the printed circuit board 405.

Safety features can be implemented in the battery module 145. For example, the printed circuit board 405 can include an analog front end (AFE) chip. The AFE chip can read cell voltages, measure current, and implement safety features (e.g., over current, short circuit, undervoltage, or overvoltage). The AFE chip can turn the charge and discharge metal-oxide-semiconductor field-effect transistors (MOSFETs) off when issues are detected, thus disconnecting the output of the pack from the cells. The printed circuit board 405 can include a microcontroller with firmware. The microcontroller can configure the AFE chip's safety limits. The microcontroller can handle error recovery, transitions, charging, discharging, and temperature limits. The microcontroller can be responsible for user interfacing. The microcontroller can be responsible for turning the charge and discharge MOSFETs on when warranted by the state machine. The microcontroller can handle fault conditions like a charger that is outputting current above a threshold and temperatures above a threshold (e.g. temperatures that are not immediately dangerous but that could lead to issues). The printed circuit board 405 can include hardware protections such as a transient-voltage suppressor (TVS) and fuse used to protect against reverse polarity, overvoltage and over current (both in charge in discharge). They can trigger if the AFE chip and the microcontroller fail at reacting to a fault. The microcontroller can run briefly (e.g., once every 10 or 100 ms) and then enter into a low power mode (e.g., drawing microamperes). The AFE chip can handle tasks that the microcontroller does not handle. This combination can allow for a low current design and a battery module 145 with a long shelf-life (e.g., more than 200 days). Communication between different components on the printed circuit board 405 can be wired or wireless (e.g., use a radio module, Bluetooth). The battery module 145 can be charged via inductive coupling or a via wire connection. The microcontroller can be connected to the serial port. The microcontroller can be connected to the battery management system 1224.

The firmware can save statistics (e.g., battery module statistics) in non-volatile memory. Battery module statistics can include number of cycles, minimum and maximum temperatures recorded, a fault counter (e.g., how many times did the battery module 145 shutdown due to short-circuit discharge or overcurrent during discharge), average mAh, average charging time, or average discharging time. The battery module 145 can communicate the battery module statistics when the battery module 145 is connected to a user application. The firmware can implement a low voltage per cell state in which the battery module 145 has a higher energy density (e.g., use 950 mAh out of the theoretical 1000 mAh maximum), but the number of charge/discharge cycles is lower before that capacity starts diminishing or before it is limited due to safety concerns. The firmware can implement a high voltage per cell state in which the battery module 145 has lower energy density (say 900 mAh) but it will support more cycles. The battery module 145 can change its position at runtime on the energy density vs. cycle life spectrum. For example, a button can be pressed that will allow a deeper discharge as compared to normal battery module operation. The firmware can control the number of charge and discharge cycles that the battery module 145 can support. The firmware can block the battery module 145 after a threshold number of cycles as a safety measure.

The exoskeleton 100 can communicate with the battery module 145 during operation. The exoskeleton 100 can use battery management system information to determine when safety measures will trigger. For example, during a high current peak (e.g., 15 A) or when the temperature is near a threshold, the power output can be turned off. The exoskeleton 100 can temporarily increase safety limits for very specific use cases (e.g., specific environmental conditions, battery life). The battery module 145 can prevent the exoskeleton 100 from shutting down by going into a low power mode and conserving power. The exoskeleton 100 can put the battery module 145 in ship mode if a major error is detected and the exoskeleton 100 wants to prevent the user from power cycling. The battery management system 1224 can be adapted to support more or less series cells, parallel cells, larger capacity cells, cylindrical cells, different lithium chemistries, etc.

Figure 5:
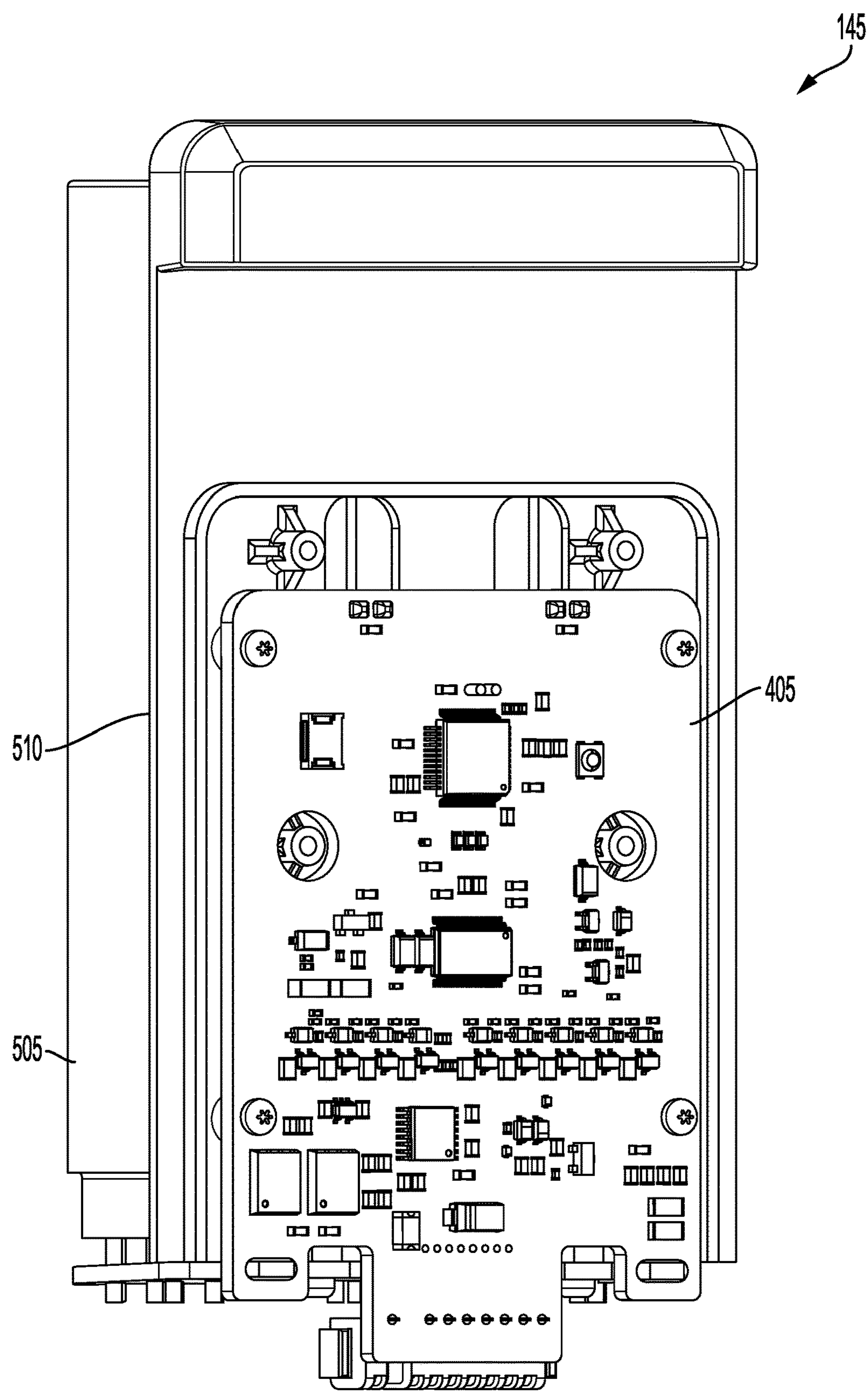
FIG. 5 illustrates a schematic diagram of a battery module, according to an embodiment.

FIG. 5 illustrates a schematic diagram of the battery module 145. The battery module 145 can include a plurality of battery cells 505. The battery module 145 can include a plurality of prismatic cells or cylindrical cells. The battery module 145 can include a plurality of prismatic lithium cells (e.g., LiPo cells, $LiFePO_4$ cells). The battery module 145 can include a plurality of prismatic $LiFePO_4$ (lithium iron phosphate) cells. The battery module 145 can include a plurality of prismatic LiPo (lithium-polymer) pouch cells. The plurality of prismatic LiPo pouch cells can deliver high power during peak loads. The plurality of prismatic LiPo pouch cells can have a higher energy density than that of cylindrical cells. The plurality of prismatic LiPo pouch cells can be packed more tightly as compared with cylindrical cells. The plurality of prismatic LiPo pouch cells can be safer than cylindrical cells in the case of a catastrophic failure of the battery module 145. The battery module 145 can include a frame 510 within a housing of the battery module 145. The battery module 145 can include the printed circuit board 405. The plurality of battery cells 505 can be soldered to the printed circuit board 405. Thermocouples can be located between each cell of the plurality of battery cells 505 to monitor the temperature of each of the cells. The battery module 145 can include a plurality of prismatic lithium cells.

Figure 6:
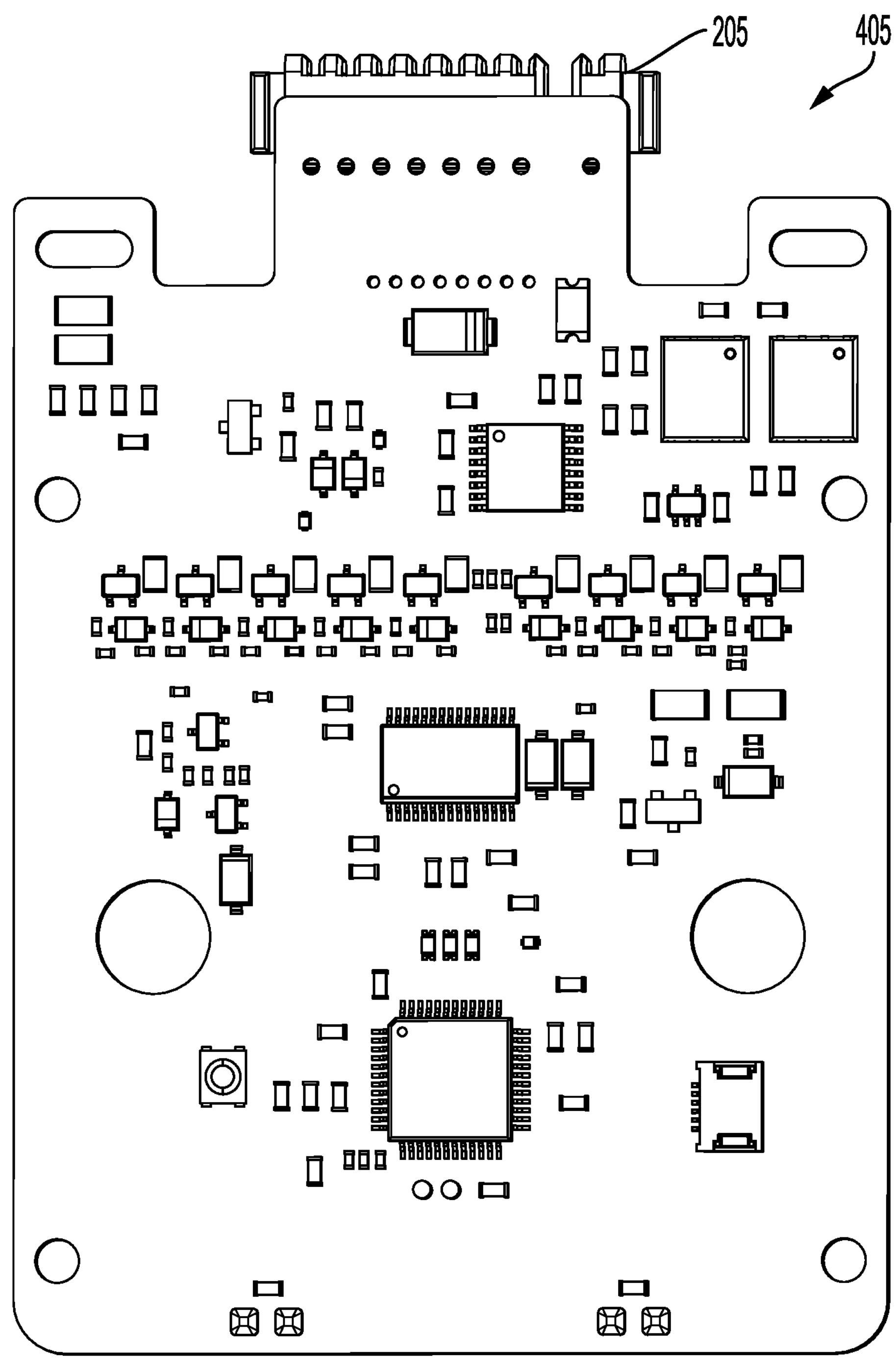
FIG. 6 illustrates a schematic diagram of a printed circuit board of a battery module, according to an embodiment.
Figure 7:
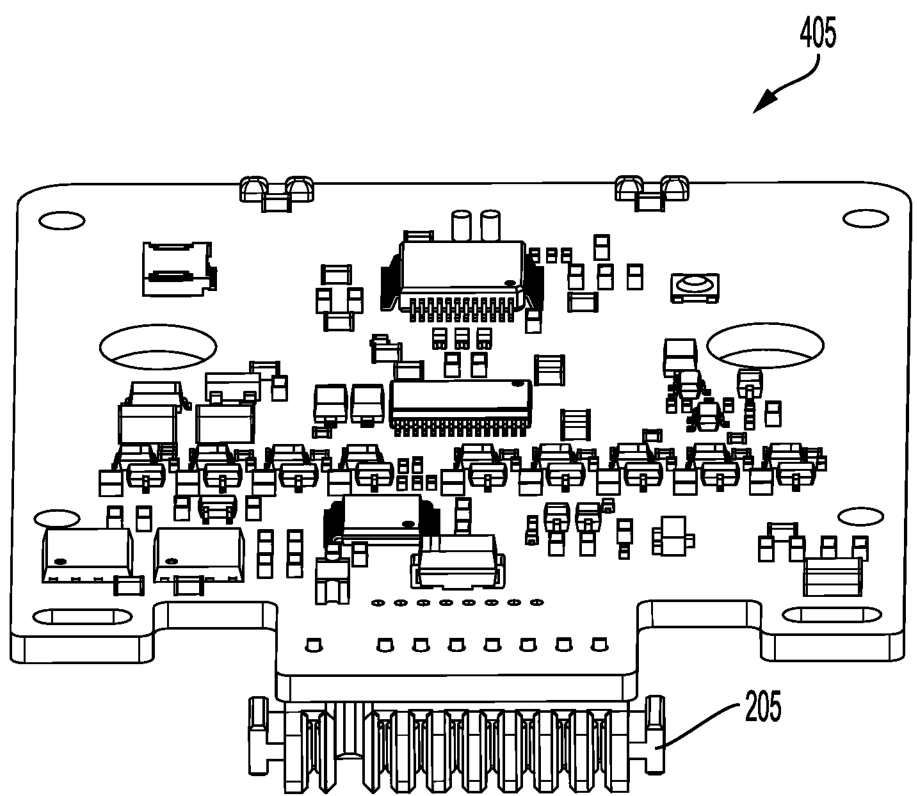
FIG. 7 illustrates a schematic diagram of the printed circuit board of a battery module, according to an embodiment.

FIGS. 6 and 7 illustrate schematic diagrams of the printed circuit board 405 of the battery module 145. The printed circuit board 405 can be soldered to the plurality of battery cells 505. The printed circuit board 405 can include a signal trace. The signal trace can electrically connect the plurality of battery cells 505 to one or more battery balancers. The printed circuit board 405 can include the first power connector 205. The first power connector 205 can be coupled to the printed circuit board 405. The printed circuit board 405 can connect the plurality of battery cells 505 in series. The printed circuit board 405 can connect the plurality of battery cells 505 in parallel.

Figure 8:
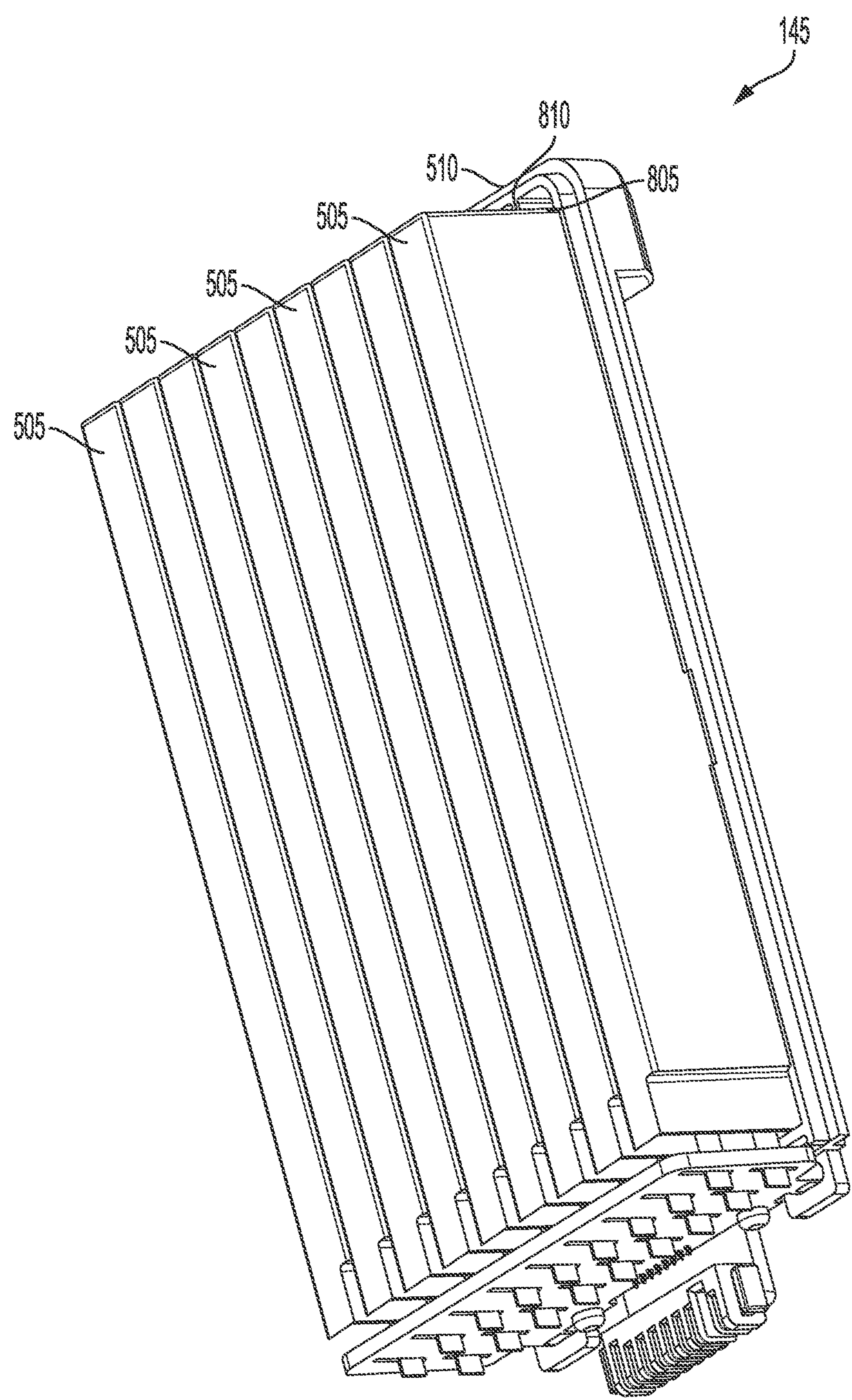
FIG. 8 illustrates a schematic diagram of a battery module, according to an embodiment.

FIG. 8 illustrates a schematic diagram of the battery module 145. The battery module 145 can include the plurality of battery cells 505 and the frame 510. An edge 805 of each of the plurality of battery cells 505 can be attached to a portion 810 of the frame 510 within the housing of the battery module 145. The plurality of battery cells 505 can be attached to the portion 810 of the frame 510 via an adhesive. The battery module 145 can include multiple battery cells 505. For example, the battery module 145 can include three to twelve battery cells 505 (e.g., eight battery cells or nine battery cells). Each of the battery cells 505 can be separated by a space allowing room for expansion. The portion 810 of the frame 510 can separate each of the plurality of battery cells 505.

Figure 9:
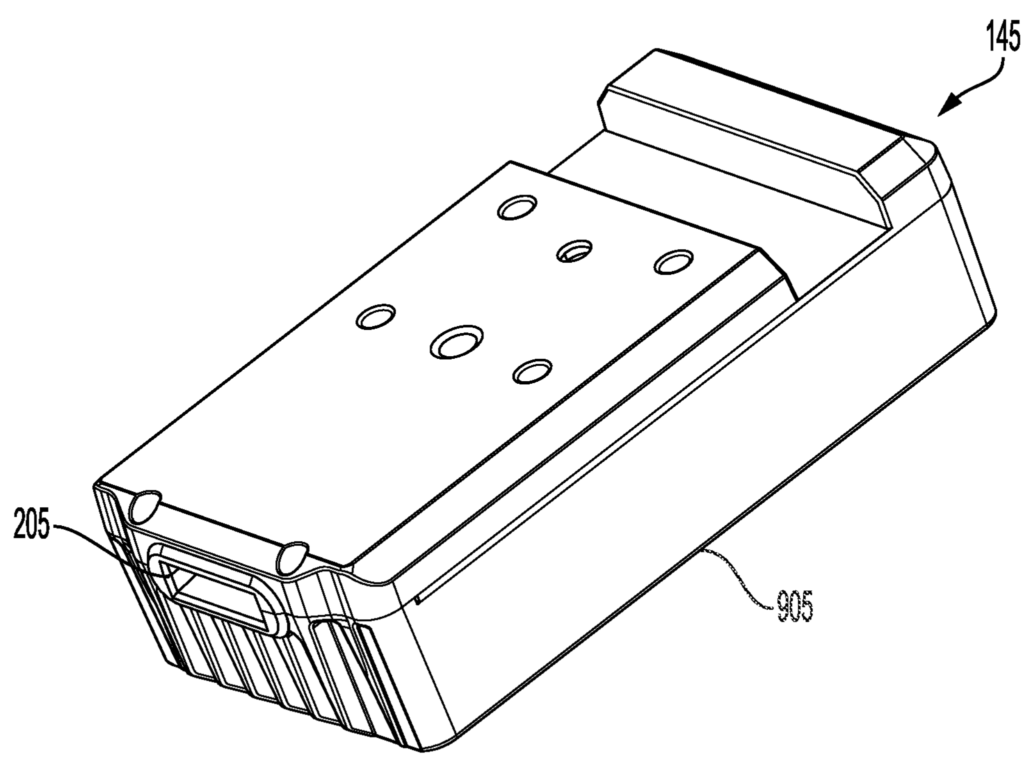
FIG. 9 illustrates a schematic diagram of a battery module, according to an embodiment.

FIG. 9 illustrates a schematic diagram of the battery module 145. The battery module 145 can include the first power connector 205. The first power connector 205 can be configured to couple with the second power connector 210. The second power connector 210 can be located in the battery holder 170 (not shown). The battery module 145 can include a chassis 905. The printed circuit board 405 and the plurality of battery cells 505 can be installed onto the chassis 905. Front and rear covers of the chassis 905 can be installed to protect the printed circuit board 405 and the plurality of battery cells 505, support the first power connector 205, and prevent water ingress. An adhesive can be located on the rear cover to support the plurality of battery cells 505. The chassis 905 can include the frame 510.

Figure 10:
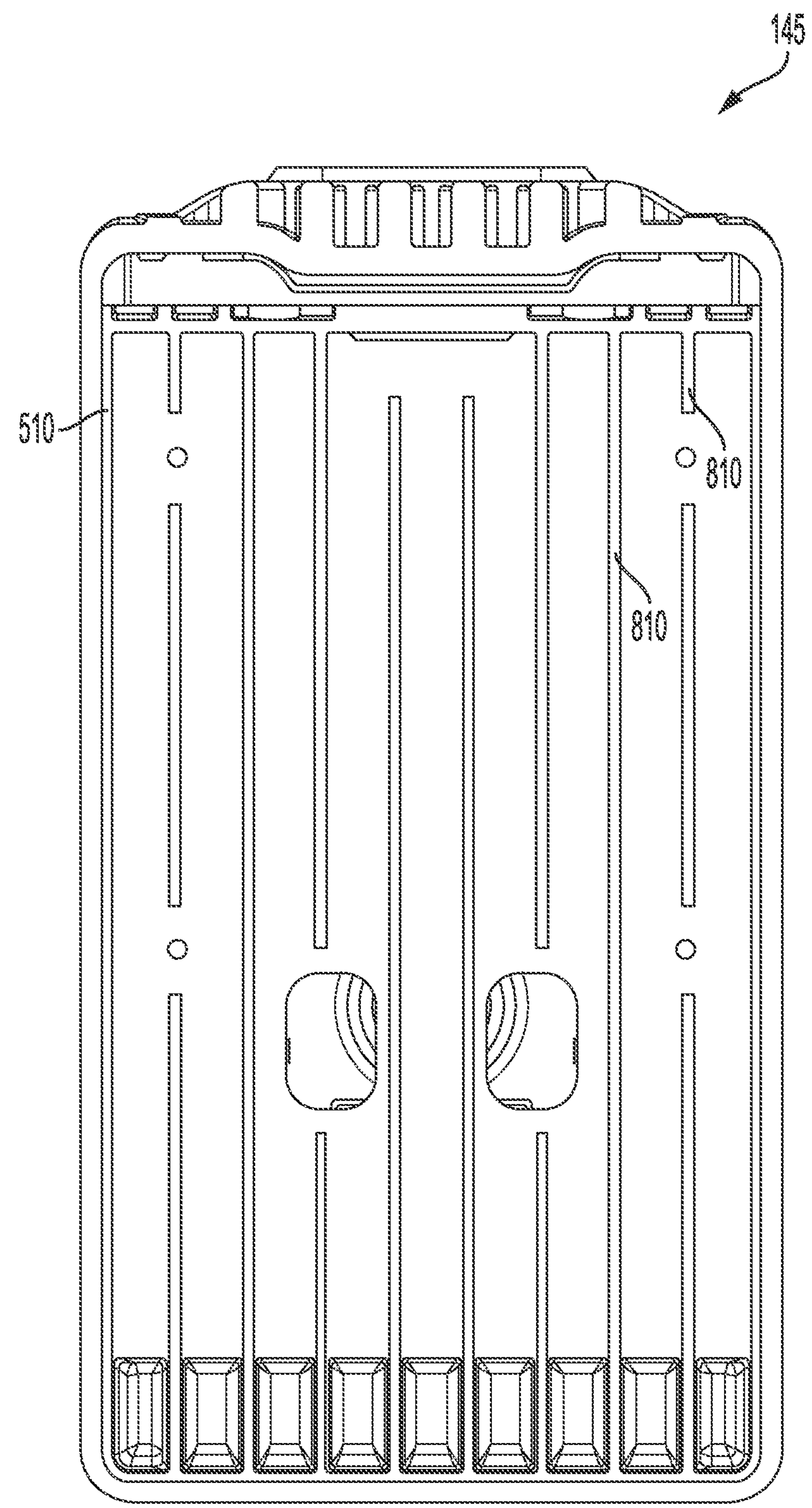
FIG. 10 illustrates a cross-section of a battery module, according to an embodiment.
Figure 11:
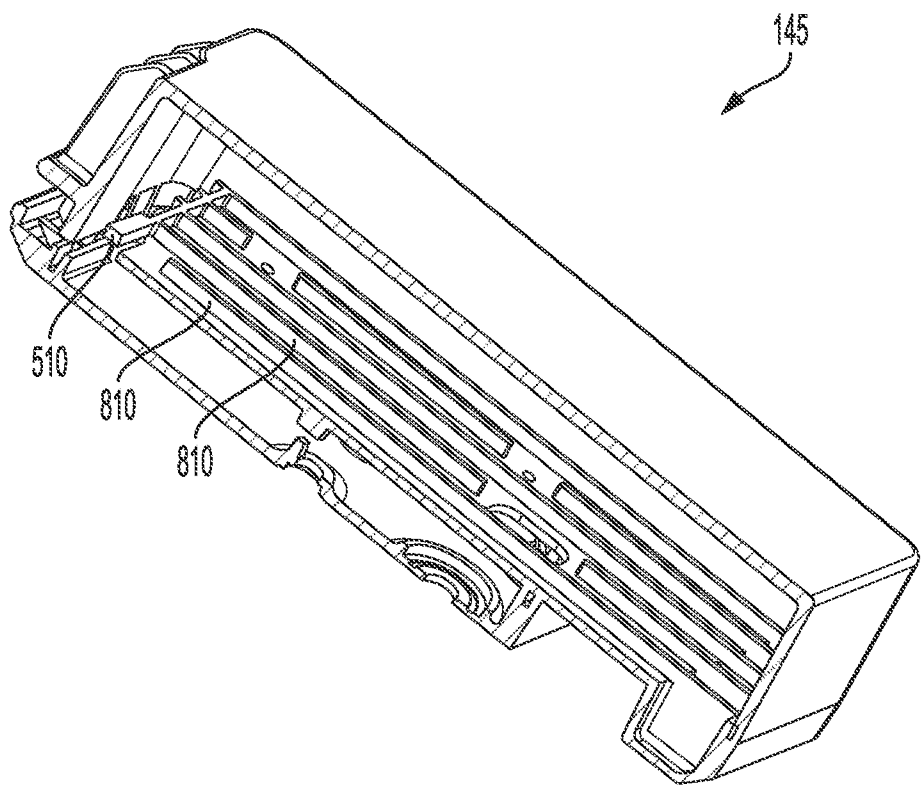
FIG. 11 illustrates a cross-section of a battery module, according to an embodiment.

FIGS. 10 and 11 illustrates cross-sections of the battery module 145. An edge 805 of each of the plurality of battery cells 505 can be attached to a portion 810 of the frame 510 within the housing of the battery module 145. The portion 810 of the frame 510 can separate each of the plurality of battery cells 505. The portion 810 of the frame 510 can provide a gap between each of the plurality of battery cells 505 to allow room for the battery cells 505 to expand during operation of the exoskeleton 100.

Figure 12A:
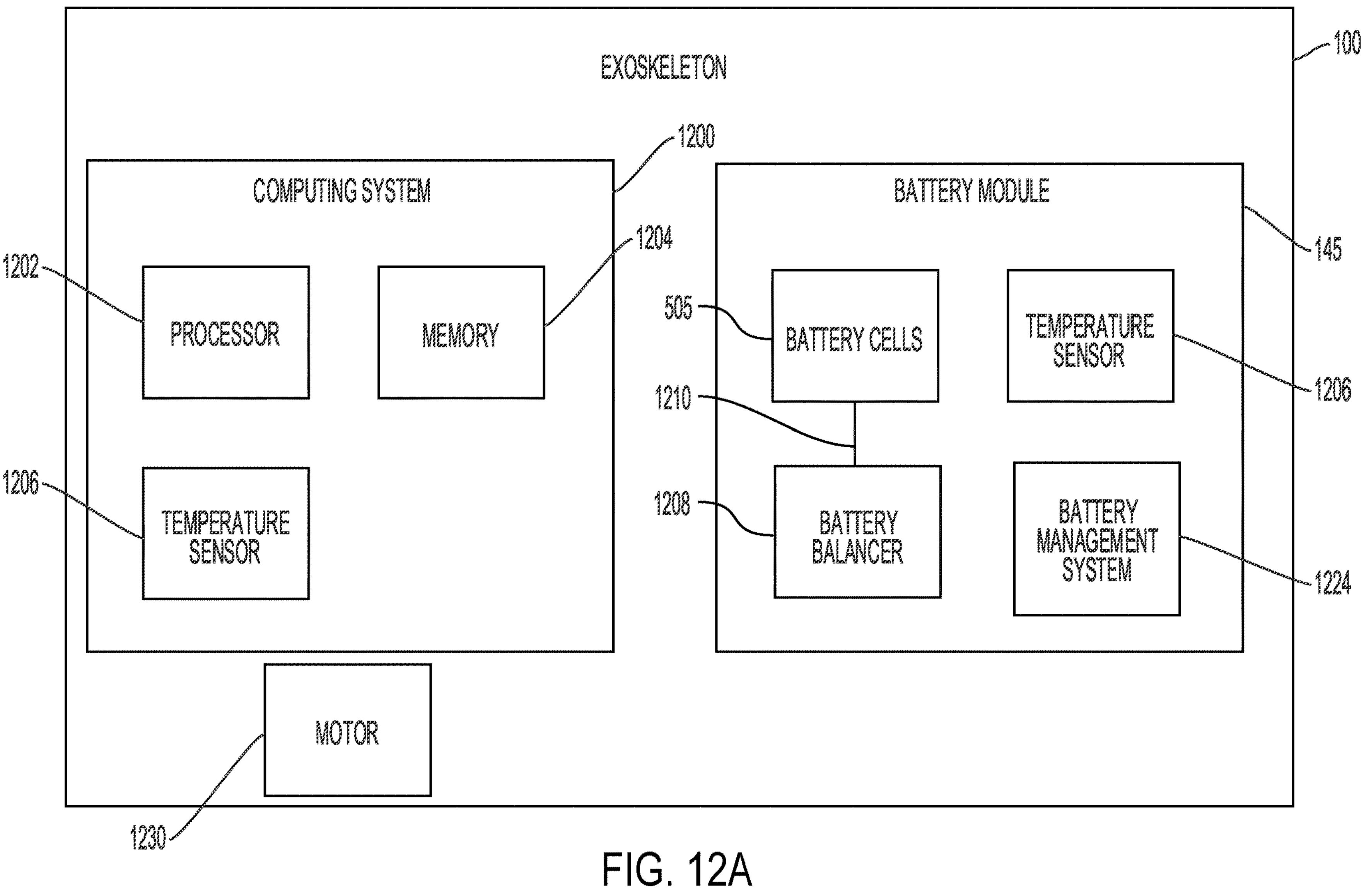
FIG. 12A illustrates a schematic diagram of an exoskeleton, according to an embodiment.

FIG. 12A illustrates a schematic diagram of an exoskeleton 100. The exoskeleton 100 can include a motor 1230. The motor 1230 can generate torque about an axis of rotation of an ankle joint of the user. The exoskeleton 100 can include the battery module 145. The exoskeleton 100 can include a computing system 1200. The exoskeleton 100 can include one or more processors 1202, memory 1204, one or more temperature sensors 106 (e.g., thermocouples), and one or more battery balancers 1208. The one or more processors 1202, memory 1204, and one or more temperature sensors 1206 can be located within the computing system 1200.

The one or more processors 1202 can receive data corresponding to a performance of the battery module 145. The data can include one or more of a temperature, current, voltage, battery percentage, internal state or firmware version. The one or more processors 1202 can determine, based on a safety policy, to trigger a safety action. The safety policy can include triggering the safety action if a threshold temperature, voltage or battery percentage is crossed. For example, the safety policy can include triggering the safety action if a temperature of one or more of the plurality of battery cells 505 is higher than a threshold temperature. The safety policy can include triggering the safety action if a battery percentage of the battery module 145 is below a threshold battery percentage. The safety policy can include triggering the safety action if a measured temperature is higher than the threshold temperature. The measured temperature can include the temperature of the printed circuit board 405 and battery cells 505. The measured temperature can include the temperature of the printed circuit board 405 and battery cells 505 measured in two locations. The safety policy can include triggering the safety action if a measured voltage is higher than the threshold voltage.

The one or more processors 1202 can instruct, based on the safety action, the electronic circuitry to adjust delivery of power from the battery module 145 to the electric motor to reduce an amount of torque generated about the axis of rotation of the ankle joint of the user. The safety action can include lowering or reducing the amount of torque generated about the axis of rotation of the ankle joint of the user. The safety action can include increasing the amount of torque generated about the axis of rotation of the ankle joint of the user.

The one or more temperature sensors 1206 can be placed between the plurality of battery cells 505 to provide an indication of a temperature between the plurality of battery cells 505. A temperature sensor of the one or more temperature sensors 1206 can be mounted on the printed circuit board 405 to measure a temperature of the printed circuit board 405. The electronic circuitry 1405 can control the delivery of power from the battery module 145 to the electric motor based at least in part on the indication of the temperature between the plurality of battery cells 505 or the temperature of the printed circuit board 405.

The one or more battery balancers 1208 can be configured to actively transfer energy from a first battery cell of the plurality of battery cells 505 to a second battery cell of the plurality of battery cells 505 having less charge than the first battery cell. A signal trace 1210 can electrically connect the plurality of battery cells 505 to the one or more battery balancers 1208. The signal trace 1210 can be located on the printed circuit board 405. The one or more battery balancers 1208 can be located within the battery module 145.

The exoskeleton 100 can include the battery module 145. The battery module 145 can include the plurality of battery cells 505, one or more temperature sensors 1206, and a battery management system 1224. The battery management system 1224 can perform various operations. For example, the battery management system 1224 can optimize the energy density of the unit, optimize the longevity of the cells, and enforce the required safety to protect the user. The battery management system 1224 can go into ship mode by electrically disconnecting the battery module 145 from the rest of the system to minimize power drain while the system is idle. The battery management system 1224 can go into ship mode if a major fault is detected. For example, if one or more of the plurality of battery cells 505 self-discharge at a rate higher than a threshold, the battery management system 1224 can re-enable the charging port.

While these components are shown as part of the exoskeleton 100, they can be located in other locations such as external to the exoskeleton 100. For example, the battery management system 1224 or the computing system 1200 can be located external to the exoskeleton 100 for testing purposes.

Figure 12B:
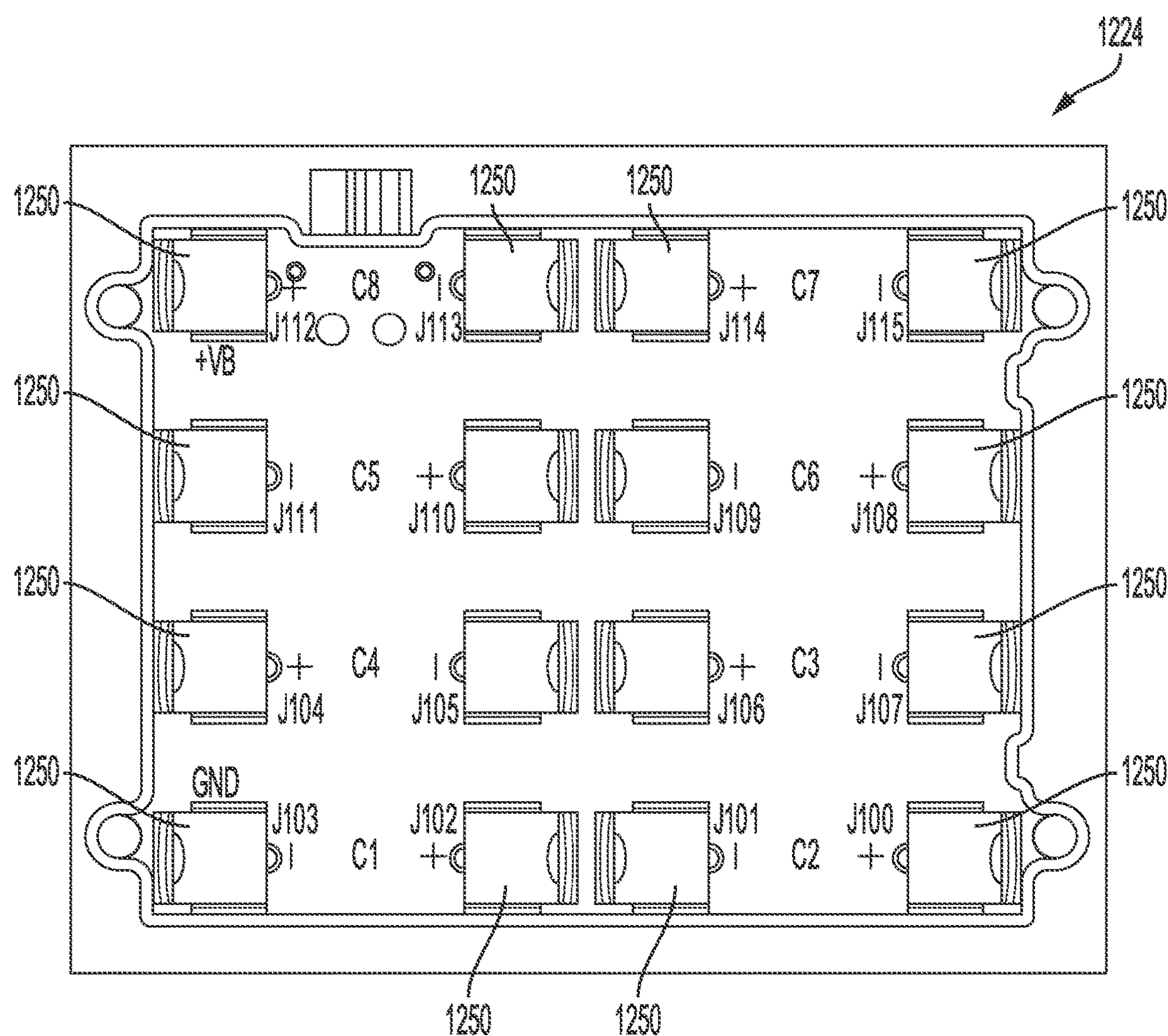
FIG. 12B illustrates a schematic diagram of a battery management system, according to an embodiment.

FIG. 12B illustrates a schematic diagram of the battery management system 1224. The battery management system 1224 can include one or more clips 1250. The one or more clips 1250 can be configured to hold one or more battery cells of the plurality of battery cells 505. For example, the one or more clips 1250 can be configured to hold one or more cylindrical cells. A battery cell of the plurality of battery cells 505 can be positioned between a first clip of the one or more clips 1250 and a second clip of the one or more clips 1250.

Figure 13:
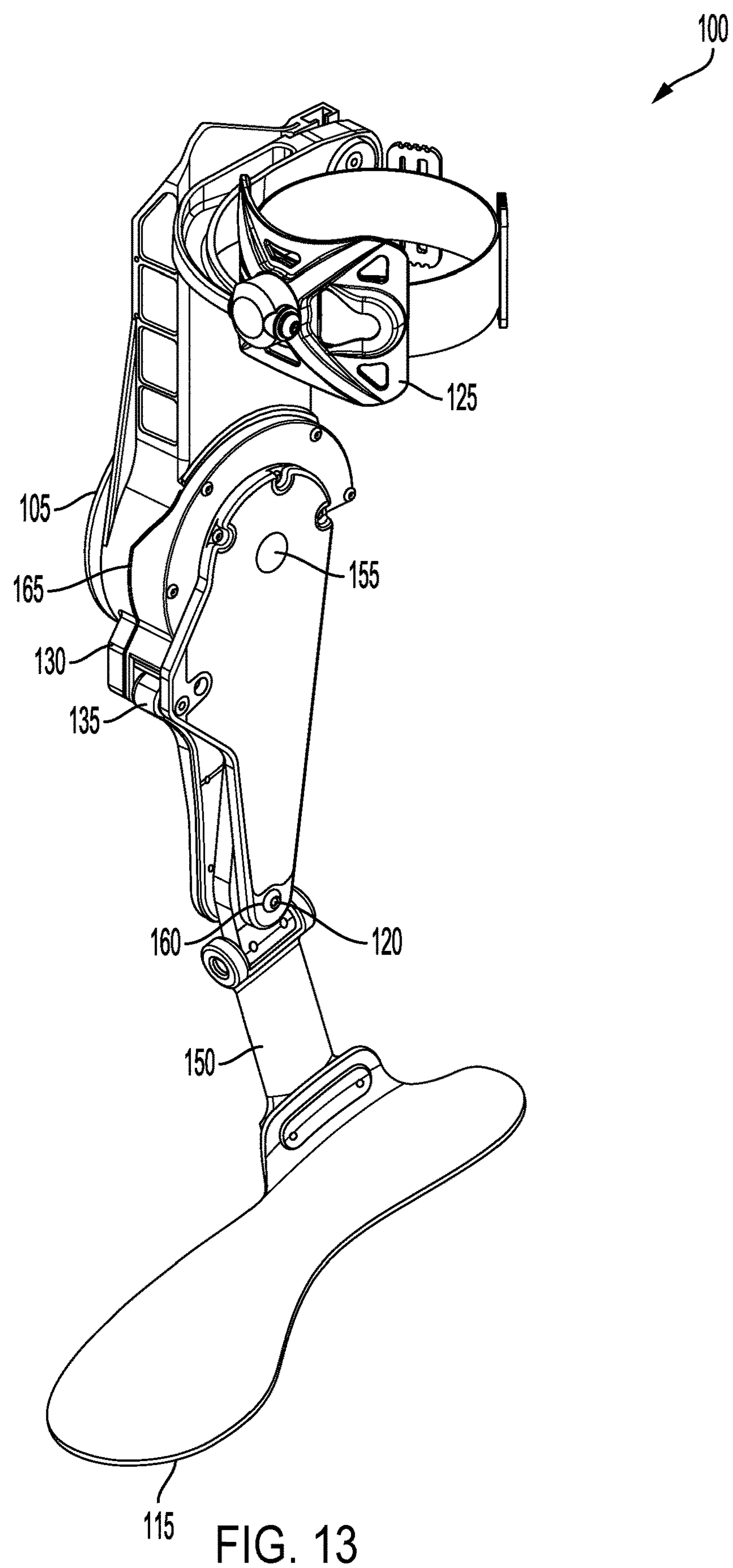
FIG. 13 illustrates a schematic diagram of an exoskeleton, according to an embodiment.

FIG. 13 illustrates a schematic diagram of the exoskeleton 100. The exoskeleton 100 can include the one or more housings 105, the footplate 115, the ankle joint component 120, shin pad 125, the actuator 130, the actuator belt 135, the post 150, the rotary encoder 155, the second rotary encoder 160, and the sealant 165 as described above. The one or more housings 105 can be coupled to the shin pad 125. The post 150 can couple the ankle joint component 120 with the footplate 115. The actuator 130 can include the one or more housings 105, the footplate 115, the ankle joint component 120, the actuator belt 135, and the post 150. The rotary encoder 155 can measure an angle of the electric motor. The second rotary encoder 160 can measure an angle of the ankle joint. The sealant 165 can be placed in contact with the one or more housings 105 to close the one or more housings 105 and prevent an ingress of water into the one or more housings 105.

Figure 14:
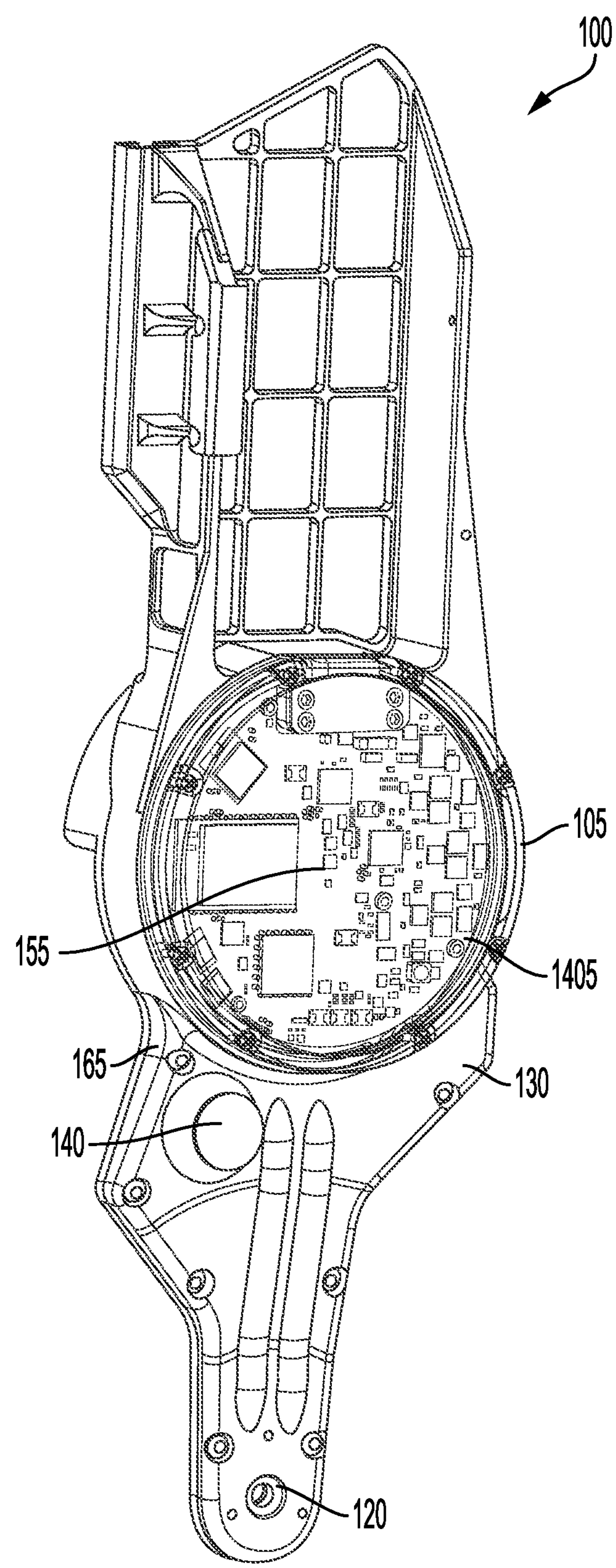
FIG. 14 illustrates a schematic diagram of the exoskeleton and internal parts, according to an embodiment.

FIG. 14 illustrates a schematic diagram of the exoskeleton 100 and internal parts. The exoskeleton 100 can include the one or more housings 105, the ankle joint component 120, the actuator 130, the power button 140, the rotary encoder 155, the second rotary encoder 160, and the sealant 165 as described above. The internal parts can include electronic circuitry 1405 (e.g., electronic circuit, circuitry, electronics). The electronic circuitry 1405 can include individual electronic components (e.g., resistors, transistors, capacitors, inductors, diodes, processors, or controllers). The power button 140 can be electrically connected to the electronic circuitry 1405. The electronic circuitry 1405 can be located behind the electric motor. The electronic circuitry 1405 can include the main electronics board. The rotary encoder 155 can be located between the motor and electronic circuitry 1405. The electronic circuitry 1405 can control delivery of power from the battery module 145 to the electric motor to generate torque about the axis of rotation of the ankle joint of the user.

Figure 15:
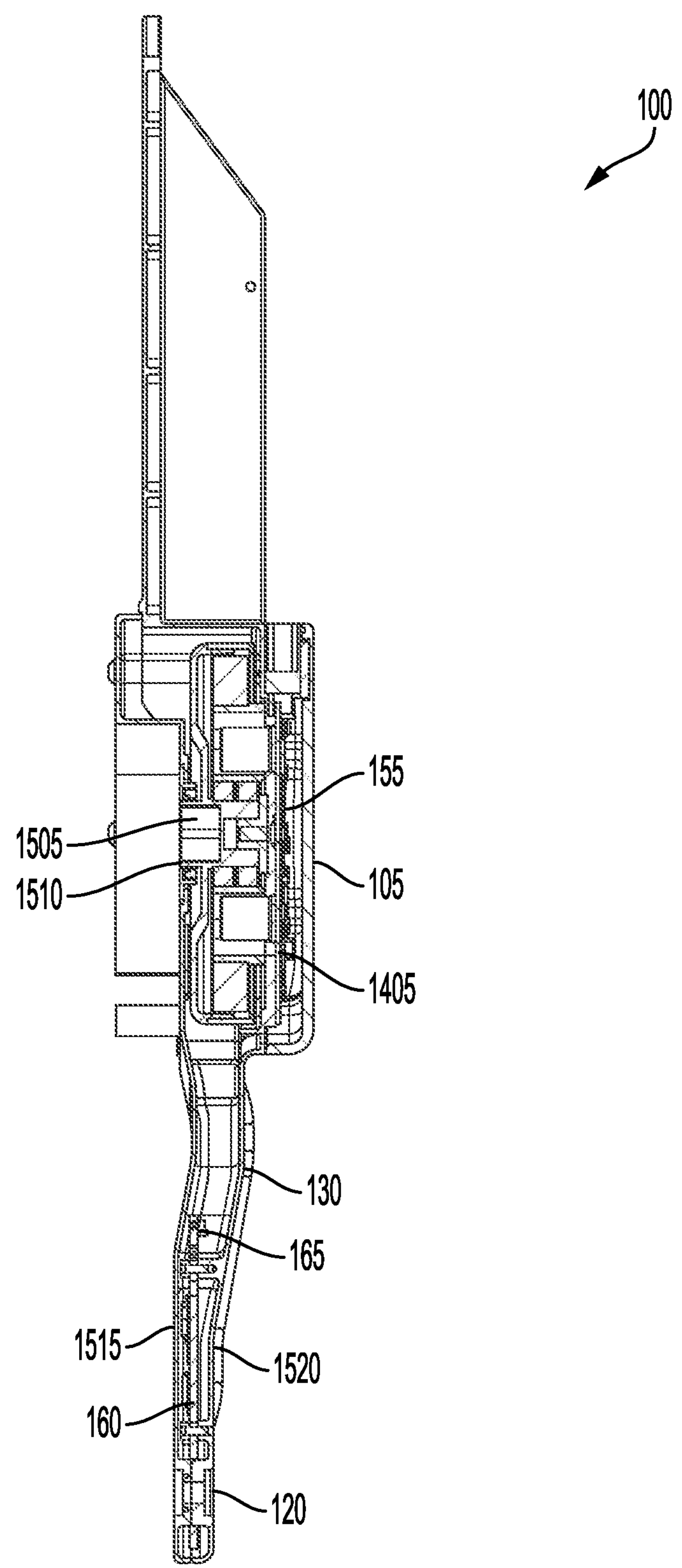
FIG. 15 illustrates a side view of an exoskeleton, according to an embodiment.

FIG. 15 illustrates a side view of the exoskeleton 100. The exoskeleton 100 can include the one or more housings 105, ankle joint component 120, the actuator 130, the rotary encoder 155, the second rotary encoder 160, the sealant 165, and electronic circuitry 1405 as described above. The exoskeleton 100 can include an output shaft 1505 (e.g., motor rotor, spool shaft, pinion gear, spur gear, or toothed pulley).

The output shaft 1505 can be coupled to the electric motor. The output shaft 1505 can extend through a bore 1510 in a housing of the one or more housings 105 enclosing the electric motor. The bore 1510 can receive the output shaft 1505. An encoder chip can be located on the electronics board on a first side of the electric motor. The encoder chip can measure the angular position of the rotary encoder 155. The exoskeleton 100 can include a transmission (e.g., gearbox) configured to couple the output shaft 1505 to the electric motor. The transmission can include a machine in a power transmission system. The transmission can provide controlled application of power. The output shaft 1505 can be integrated into the motor rotor. The output shaft 1505 can be part of a mechanism (e.g., gears, belts, linkage, or change). An ankle shaft can extend through the second rotary encoder 160 which can increase the structural integrity of the exoskeleton 100.

The exoskeleton 100 can include a first component of the fitted structure 1515 (e.g., first clamshell structure). The exoskeleton 100 can include a second component of the fitted structure 1520 (e.g., second clamshell structure). The first component of the fitted structure 1515 can be coupled with the second component of the fitted structure 1520. The first component of the fitted structure 1515 can be attached to the second component of the fitted structure 1520 via the sealant 165 (e.g., adhesive sealant). The first component of the fitted structure 1515 can be coupled to the second component of the fitted structure 1520 such that the fitting prevents or decreases a rate of water flow into the interior of the exoskeleton 100. The fitted structure can include two or more components such that the assembly components prevents or decreases a rate of water flow into the interior of the exoskeleton 100. The first component of the fitted structure 1515 and the second component of the fitted structure 1520 can be stationary components. The number of individual components of the fitted structure can be minimized to decrease the number of possible entry points for water to enter the exoskeleton 100. The possible entry points can include seams and/or moving parts of the exoskeleton 100. The seams can be permanently sealed via the sealant 165.

An adhesive sealant (e.g., super glue, epoxy resin, or polyvinyl acetate) can be placed between the first component of the fitted structure 1515 and the second component of the fitted structure 1520. The adhesive sealant can prevent or decrease the rate of water flow through the seam between the first component of the fitted structure 1515 and the second component of the fitted structure 1520 into the interior of the exoskeleton 100. The adhesive sealant can be placed under the electronics cover. The adhesive sealant can prevent or decrease the rate of water flow through the seam between the electronics cover and the exoskeleton one or more housings 105 into the interior of the exoskeleton 100.

A gasket can be placed between the first component of the fitted structure 1515 and the second component of the fitted structure 1520. The gasket can be placed in the seam between the first component of the fitted structure 1515 and the second component of the fitted structure 1520. The gasket can prevent or decrease the rate of water flow through the seam between the first component of the fitted structure 1515 and the second component of the fitted structure 1520.

Figure 16:
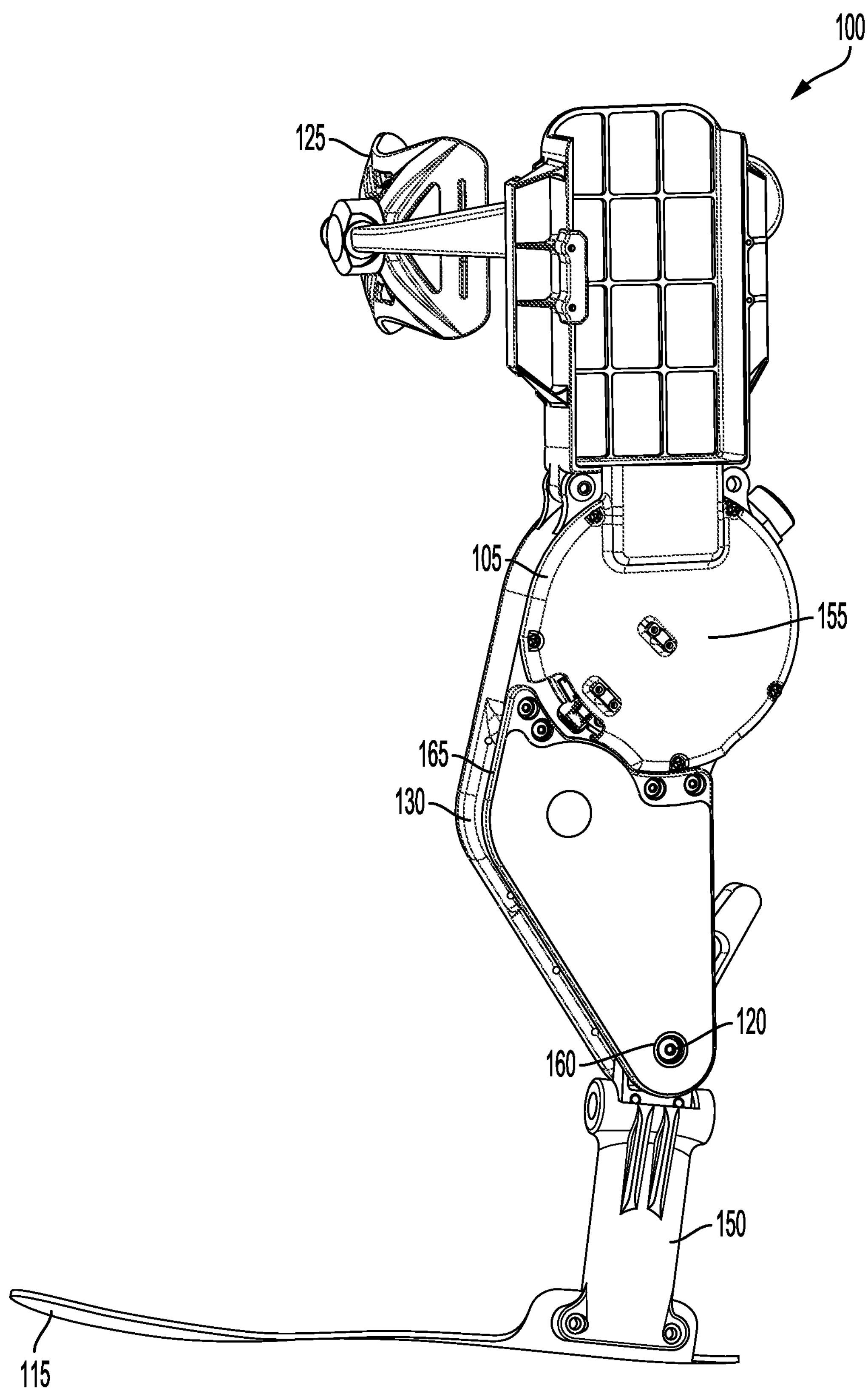
FIG. 16 illustrates a schematic diagram of an exoskeleton, according to an embodiment.

FIG. 16 illustrates a schematic diagram of the exoskeleton 100. The exoskeleton 100 can include the one or more housings 105, the footplate 115, the ankle joint component 120, the shin pad 125, the actuator 130, the post 150, the rotary encoder 155, the second rotary encoder 160, and the sealant 165 as described above. The one or more housings 105 can be coupled to the shin pad 125. The post 150 can couple the ankle joint component 120 with the footplate 115. The actuator 130 can include the one or more housings 105, the footplate 115, the ankle joint component 120, and the post 150. The rotary encoder 155 can measure an angle of the electric motor. The second rotary encoder 160 can measure an angle of the ankle joint.

Figure 17:
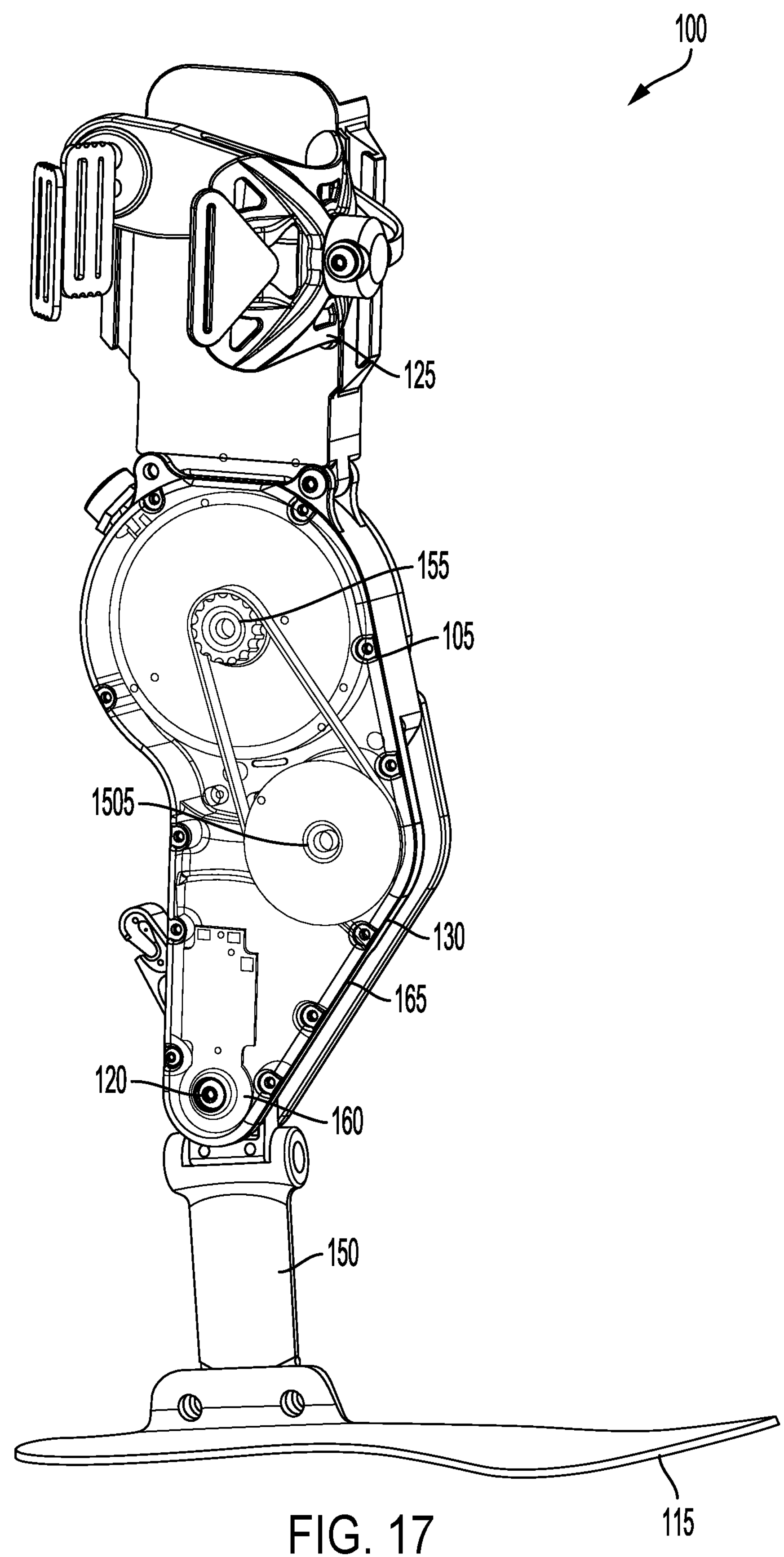
FIG. 17 illustrates a schematic diagram of an exoskeleton and internal parts, according to an embodiment.
Figure 18:
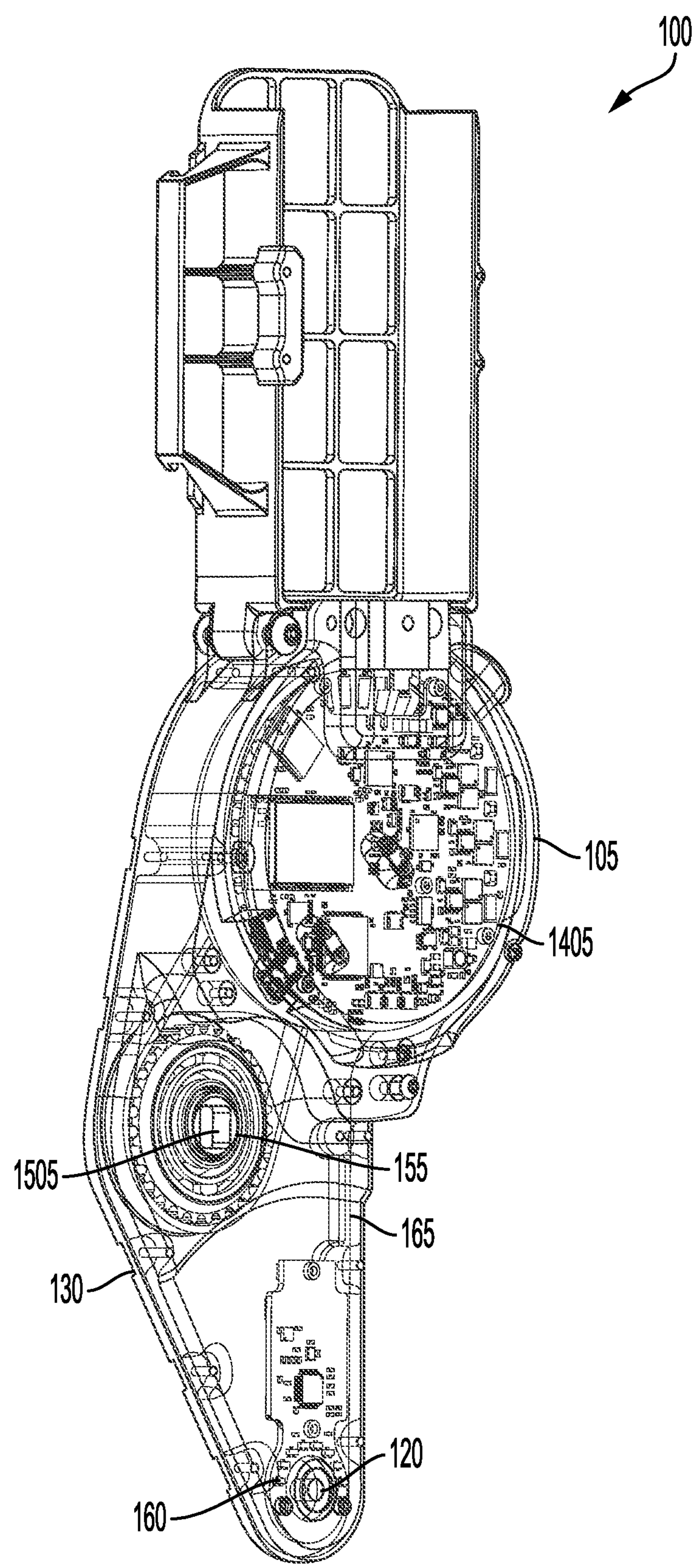
FIG. 18 illustrates a schematic diagram of an exoskeleton and internal parts, according to an embodiment.

FIG. 17 and FIG. 18 illustrate schematic diagrams of the exoskeleton 100 and internal parts. The exoskeleton 100 can include the one or more housings 105, the footplate 115, the ankle joint component 120, shin pad 125, the actuator 130, the post 150, the rotary encoder 155, the second rotary encoder 160, the sealant 165, and electronic circuitry 1405 as described above. The internal parts can include an electronic circuit (e.g., circuitry). The electronic circuit can include individual electronic components (e.g., resistors, transistors, capacitors, inductors, diodes, processors, or controllers). The motor rotor can be connected to the output shaft 1505.

Figure 19:
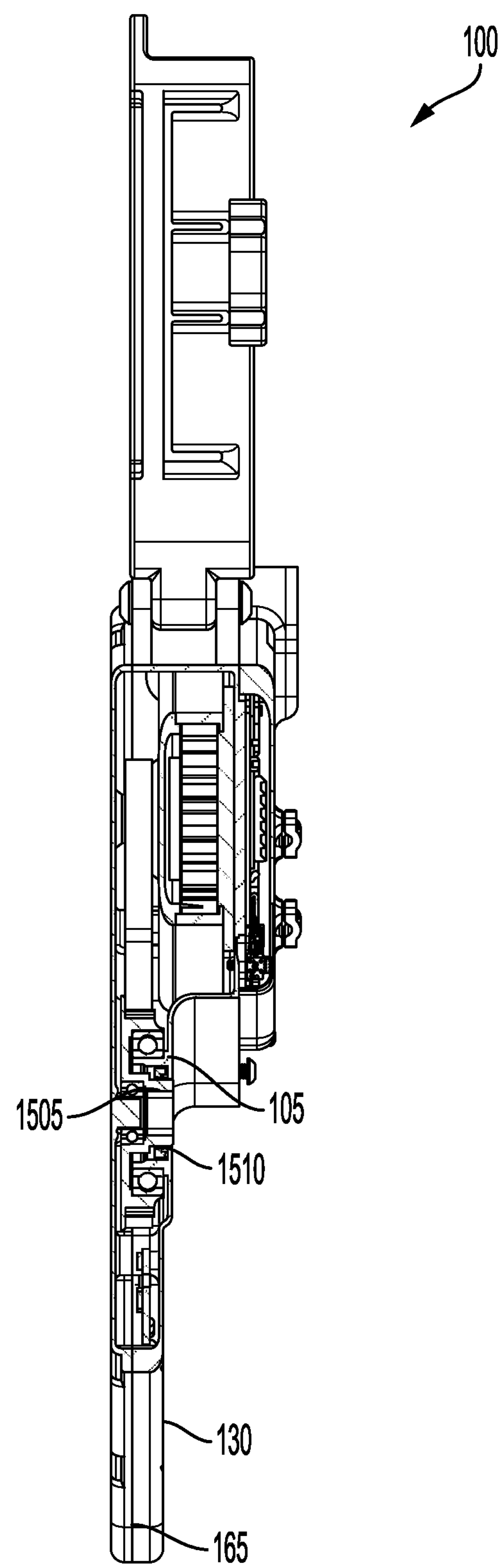
FIG. 19 illustrates a side view of an exoskeleton, according to an embodiment.

FIG. 19 illustrates a side view of the exoskeleton 100. The exoskeleton 100 can include the one or more housings 105, the actuator 130, the rotary encoder 155, the second rotary encoder 160, and the sealant 165, the output shaft 1505, and the bore 1510 as described above. The exoskeleton 100 can include an output shaft 1505 (e.g., motor rotor). The output shaft 1505 can be coupled to the electric motor. The output shaft 1505 can extend through a bore 1510 in a housing of the one or more housings 105 enclosing the electric motor. The bore 1510 can receive the output shaft 1505. A magnet can be located on a first side of the electric motor. An encoder chip can be located on the electronics board on the first side of the electric motor. The encoder chip can measure the angular position of the rotary encoder 155. An ankle shaft can extend through the second rotary encoder 160 which can increase the structural integrity of the exoskeleton 100. The exoskeleton 100 can include a transmission (e.g., gearbox) configured to couple the output shaft 1505 to the electric motor. The transmission can include a machine in a power transmission system. The transmission can provide controlled application of power.

Figure 20:
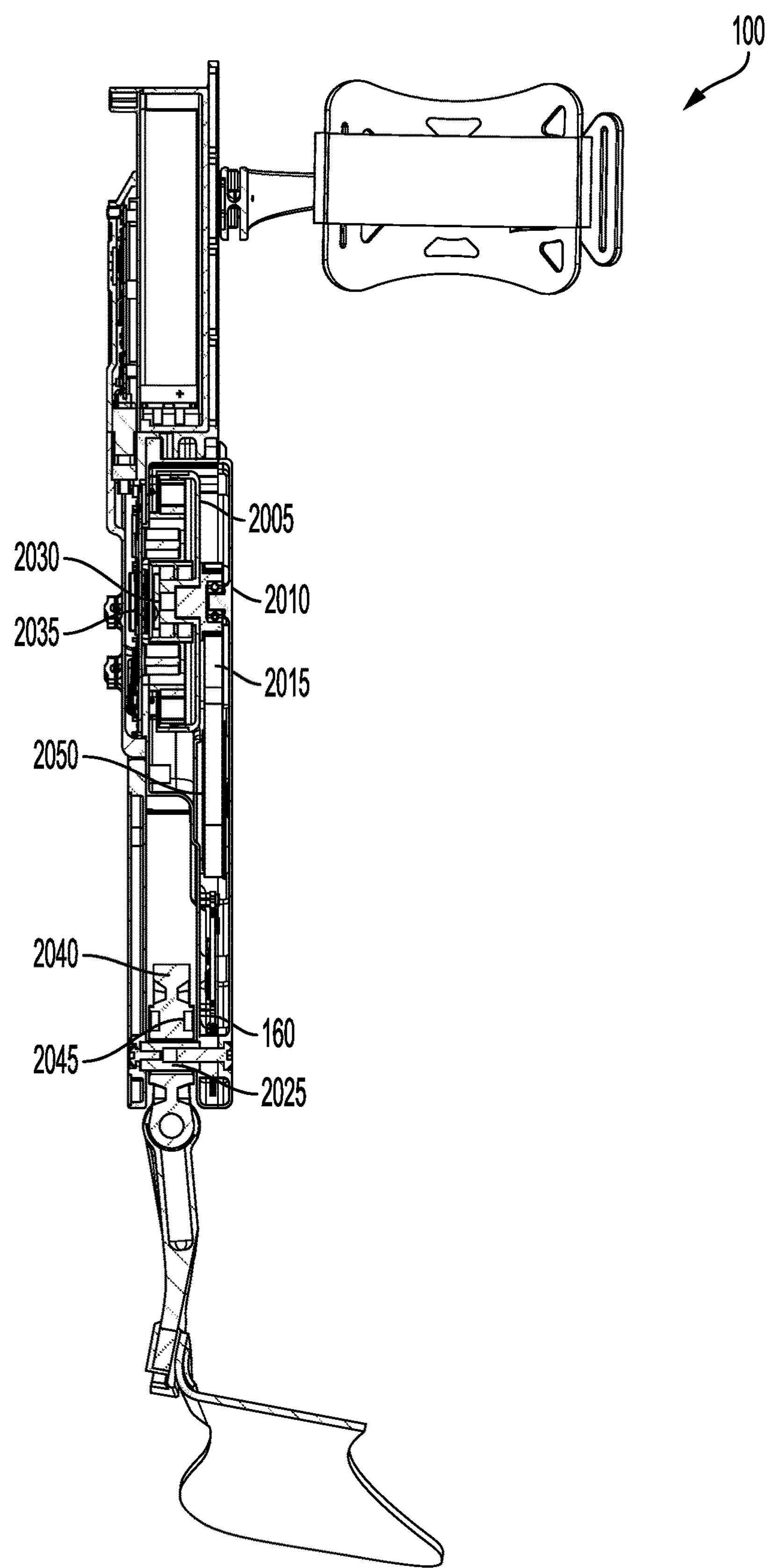
FIG. 20 illustrates a side view of an exoskeleton, according to an embodiment.

FIG. 20 illustrates a side view of an exoskeleton 100. The exoskeleton 100 can include a motor 2005 (e.g., electric motor), a motor timing pulley 2010 (e.g., timing pulley), a motor timing belt 2015 (e.g., timing belt), the second rotary encoder 160 (e.g., an ankle encoder PCB, ankle encoder printed circuit board, second rotary encoder PCB, or ankle encoder), an ankle shaft 2025, a motor encoder magnet 2030, a motor encoder 2035, a lever arm 2040 (e.g., ankle lever), and an ankle encoder magnet 2045. The ankle shaft 2025 can extend through the second rotary encoder 160 to increase the structural integrity of the exoskeleton 100. The motor timing belt 2015 can be coupled to a sprocket 2050. The sprocket 2050 can be coupled with a spool. The motor encoder magnet 2030 can be located on the first side of the electric motor.

Figure 21:
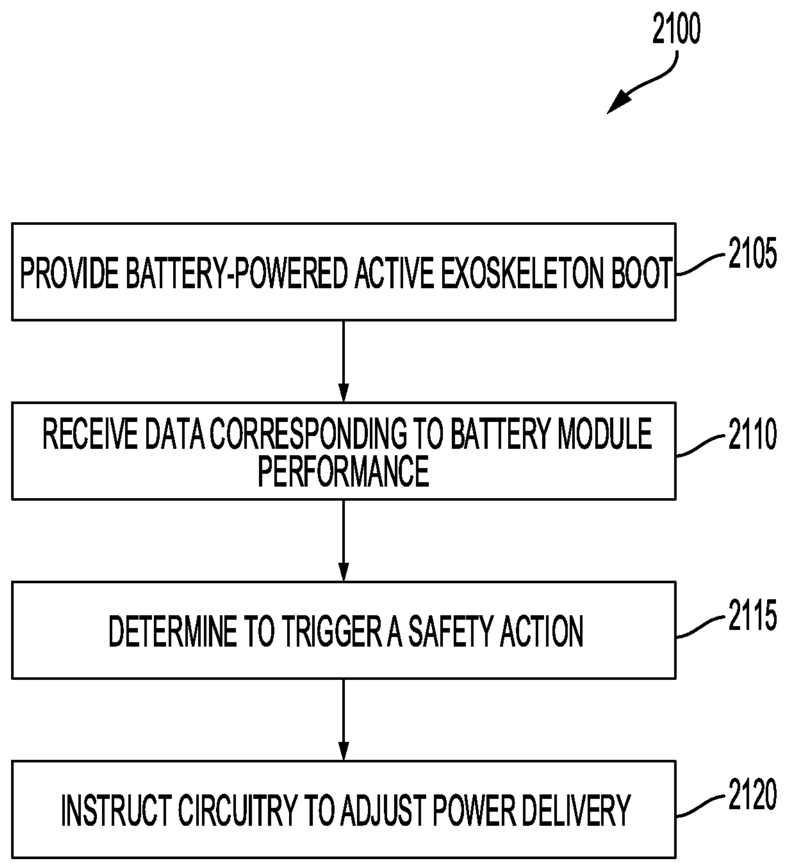
FIG. 21 illustrates a method of augmenting user motion, according to an embodiment.
Figure 22:
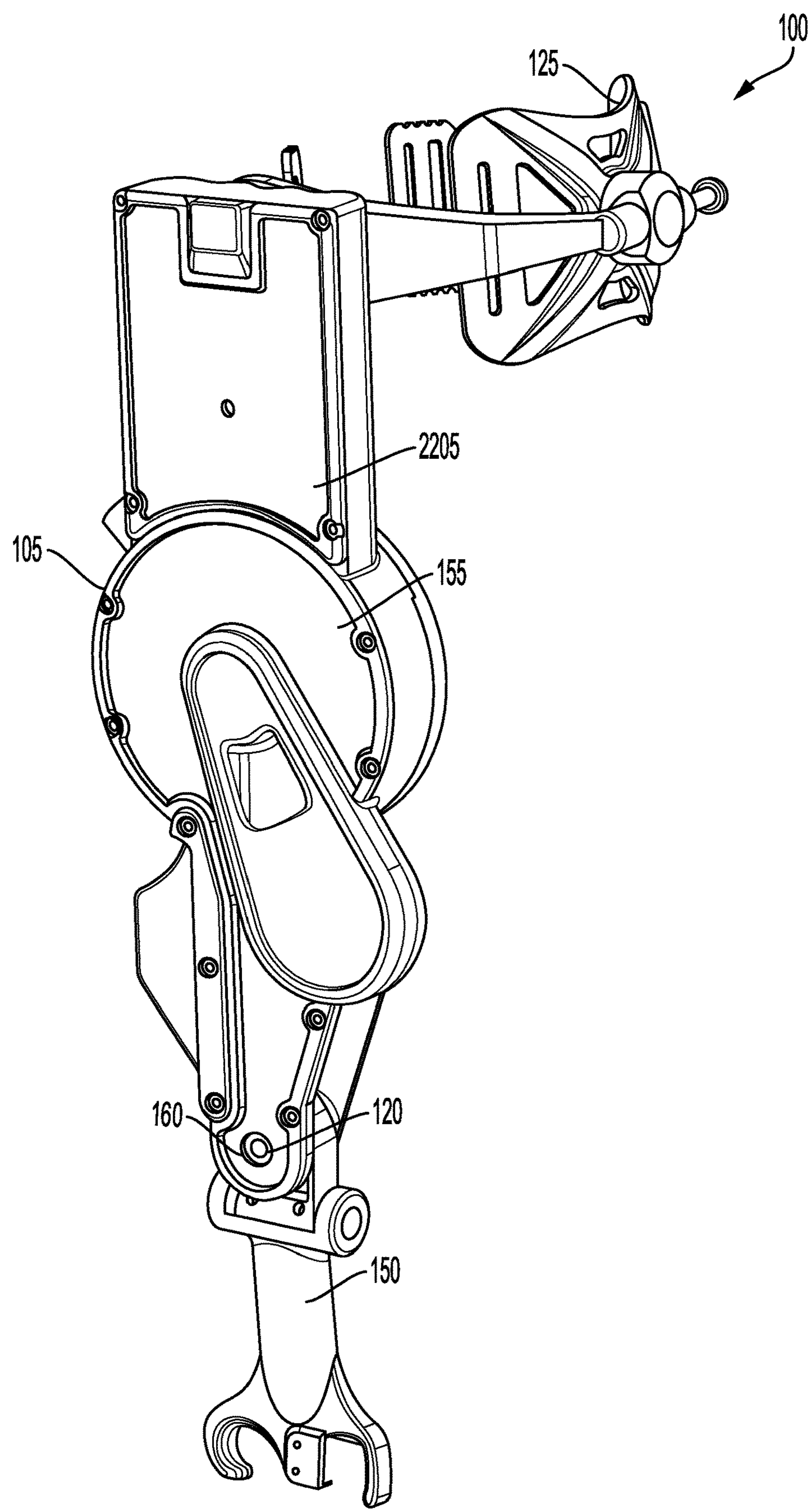
FIG. 22 illustrates a schematic diagram of the exoskeleton and an integrated battery module, according to an embodiment.

FIG. 21 illustrates a method 2100 of augmenting user motion. The method 2100 can include providing, to a user, a battery-powered active exoskeleton boot (BLOCK 2105). The battery-powered active exoskeleton boot can include a shin pad to be coupled to a shin of a user below a knee of the user. The battery-powered active exoskeleton boot can include one or more housings enclosing electronic circuitry and an electric motor that can generate torque about an axis of rotation of an ankle joint of the user. At least one of the one or more housings can be coupled to the shin pad below the knee of the user. The battery-powered active exoskeleton boot can include a battery holder coupled to the shin pad. The battery holder can be located below the knee of the user and above the one or more housings enclosing the electronic circuitry. The battery-powered active exoskeleton boot can include a battery module removably affixed to the battery holder. The battery module can include a first power connector that electrically couples to a second power connector located in the battery holder while attached to the battery holder to provide electric power to the electronic circuitry and the electric motor. The battery-powered active exoskeleton boot can include an output shaft coupled to the electric motor and extending through a bore in a housing of the one or more housings enclosing the electric motor. The electronic circuitry can control delivery of power from the battery module to the electric motor to generate torque about the axis of rotation of the ankle joint of the user.

In some embodiments, the first power connector includes a blade connector. The second power connector can include a receptacle configured to receive the blade connector absent an exposed cable. The battery module can include a plurality of battery cells. The battery module can include a printed circuit board soldered to the plurality of battery cells. The battery module can include one or more battery balancers configured to actively transfer energy from a first battery cell of the plurality of battery cells to a second battery cell of the plurality of battery cells having less charge than the first battery cell. The battery module can include a signal trace, on the printed circuit board, that electrically connects the plurality of battery cells to the one or more battery balancers.

In some embodiments, the method 2100 includes providing, via a serial data communication port of the first power connector, at least one of battery state data, a battery test function, a smart charging function, or a firmware upgrade. The battery state data can include the health of the battery module. The battery test function can include probing the battery module. The smart charging function can include using a high voltage to charge the battery module. A pin of the first power connector that provides serial data can be further configured to receive a voltage input greater than or equal to a threshold to wake up a battery management system of the battery module. The pin can be configured to receive a voltage input greater than or equal to a threshold to put the battery management system to sleep. The pin can be configured to receive a voltage input greater than or equal to a threshold to put the battery management system in a bootloader mode.

The method 2100 can include receiving data corresponding to battery module performance (BLOCK 2110). For example, the method 2100 can include receiving, by one or more processors of the battery-powered active exoskeleton boot, data corresponding to a performance of the battery module, the data comprising one or more of a temperature, current, voltage, battery percentage. For example, the data can include a temperature from one or more temperature sensors of the computing system. The data can include a temperature from one or more temperature sensors of the battery module.

The method 2100 can include determining to trigger a safety action (BLOCK 2115). For example, the method 2100 can include determining, by the one or more processors, based on a safety policy, to trigger a safety action. The safety policy can include triggering the safety action if a threshold temperature, voltage or battery percentage is crossed. For example, the safety policy can include triggering the safety action if a temperature of one or more of the plurality of battery cells is higher than a threshold temperature. The safety policy can include triggering the safety action if a battery percentage of the battery module is below a threshold battery percentage. The measured temperature can include the temperature of the printed circuit board and battery cells. The measured temperature can include the temperature of the printed circuit board and battery cells measured in two locations. The safety policy can include triggering the safety action if a measured voltage is higher than the threshold voltage.

The method 2100 can include instructing circuitry to adjust power delivery (BLOCK 2120). For example, the method 2100 can include instructing, by the one or more processors, based on the safety action, the electronic circuitry to adjust delivery of power from the battery module to the electric motor to reduce an amount of torque generated about the axis of rotation of the ankle joint of the user. The safety action can include lowering or reducing the amount of torque generated about the axis of rotation of the ankle joint of the user. The safety action can include increasing the amount of torque generated about the axis of rotation of the ankle joint of the user.

FIGS. 22-25 illustrate a schematic diagrams of the exoskeleton 100 and an integrated battery module 2205. The exoskeleton 100 can include the one or more housings 105, the ankle joint component 120, the shin pad 125, the post 150, the rotary encoder 155, the second rotary encoder 160, the printed circuit board 405, the plurality of battery cells 505, the one or more clips 1250, and the battery holder 170 as described above. The one or more housings 105 can be coupled to the shin pad 125. The rotary encoder 155 can measure an angle of the electric motor. The second rotary encoder 160 can measure an angle of the ankle joint. The plurality of battery cells 505 can include cylindrical cells.

The exoskeleton 100 can include the integrated battery module 2205 (e.g., integrated battery). The integrated battery module 2205 can be integrated with the exoskeleton 100. The integrated battery module 2205 can be part of the exoskeleton. For example, the integrated battery module 2205 and the one or more housings 105 can be formed of one piece, as opposed to a removable battery module that is not integrated with the one or more housings 105. The removable battery module can include a battery module whereby the plurality of battery cells 505 are enclosed in a casing that is configured to slide out of the battery holder 170. The integrated battery module 2205 can include a battery module whereby each of the plurality of battery cells 505 are configured to be positioned between the one or more clips 1250. The integrated battery module 2205 can be permanently attached to the one or more housings 105 of the exoskeleton 100. For example, the integrated battery module 2205 may not be removable. The battery cells of the integrated battery module 2205 can be soldered or otherwise coupled or affixed to the PCB or portion of the exoskeleton 100.

Figure 23:
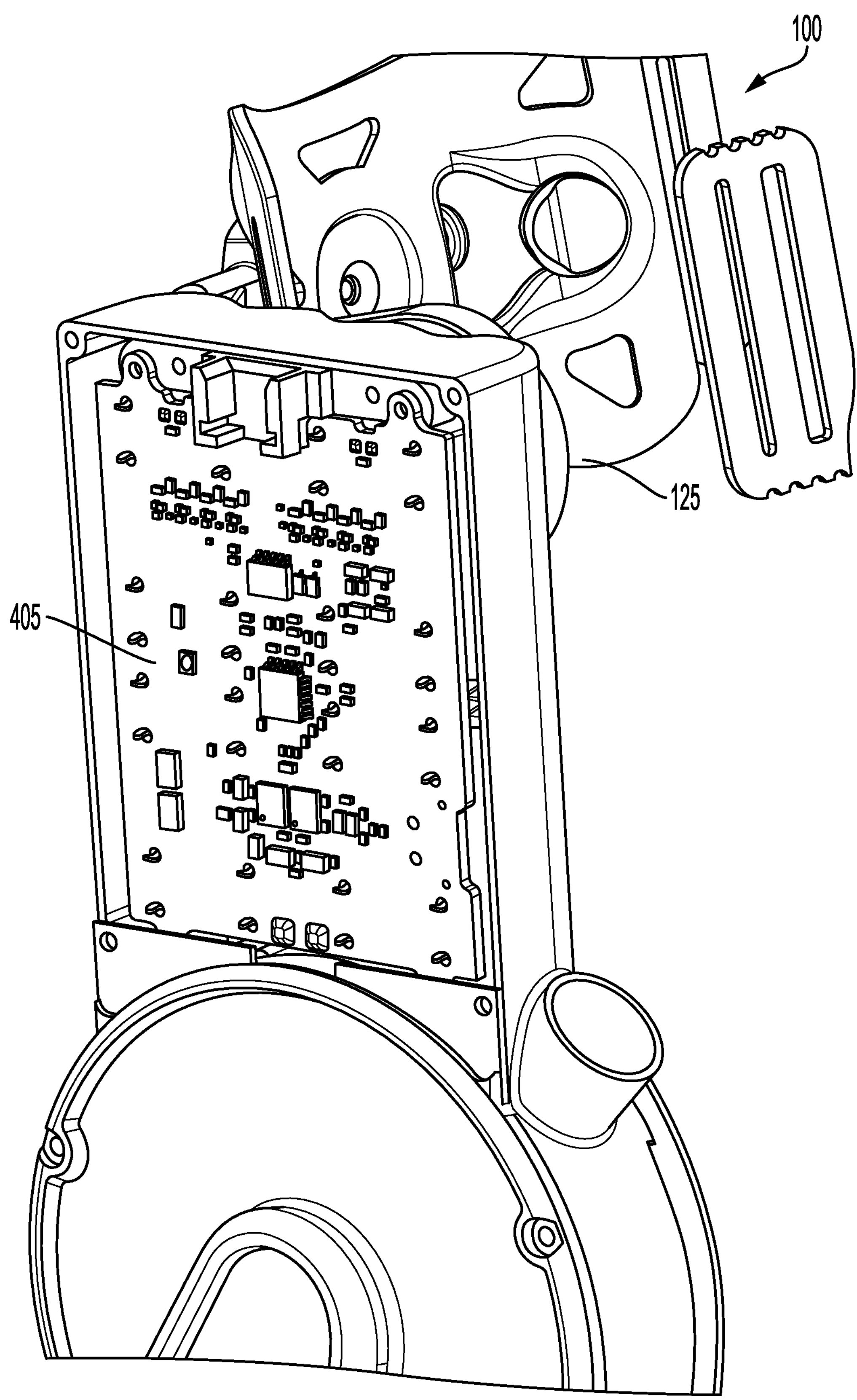
FIG. 23 illustrates a schematic diagram of the exoskeleton and an integrated battery module, according to an embodiment.

FIG. 23 illustrates a PCB 405 that is integrated to the exoskeleton, in accordance with implementations. The PCB 405 can be the exterior side (e.g., the side of the exoskeleton opposite the side of the exoskeleton adjacent to the leg of a user) of the exoskeleton, while the integrated battery module 2205 can be on the interior of the exoskeleton 100. In some cases, the integrated battery module 2205 can be on the exterior of the exoskeleton 100 while the PCB 405 can be on the interior of the exoskeleton 100.

Figure 24:
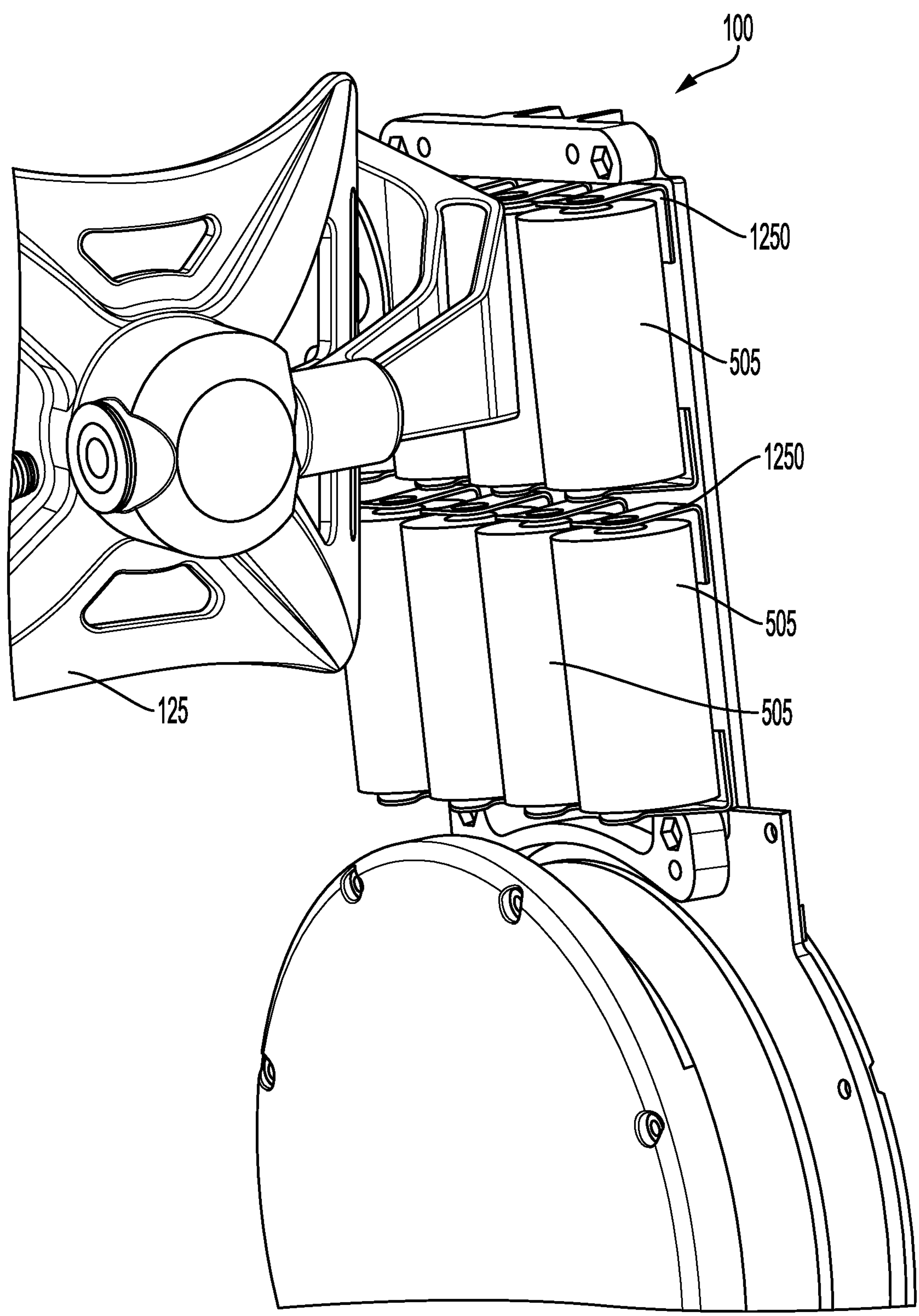
FIG. 24 illustrates a schematic diagram of the exoskeleton and an integrated battery module, according to an embodiment.

FIG. 24 depicts battery cells 505 that are integrated with the exoskeleton 100, in accordance with implementations. The battery cells 505 can be directly coupled or affixed to a portion of the exoskeleton or PCB 405. The battery cells 505 can be coupled using solder, an adhesive, or fasteners to a portion of the PCB 405 or clips configured to hold the battery cells 505 to a portion of the exoskeleton 100. The battery cells 505 can be coupled to a side of the exoskeleton 100 that is adjacent to the shin pad 125. For example, the integrated battery cells 505 can be located in between the shin pad 125 and the PCB 405, whereas in the removable battery module configuration, the PCB 405 can be located in between the shin pads 125 and the battery module.

Figure 25:
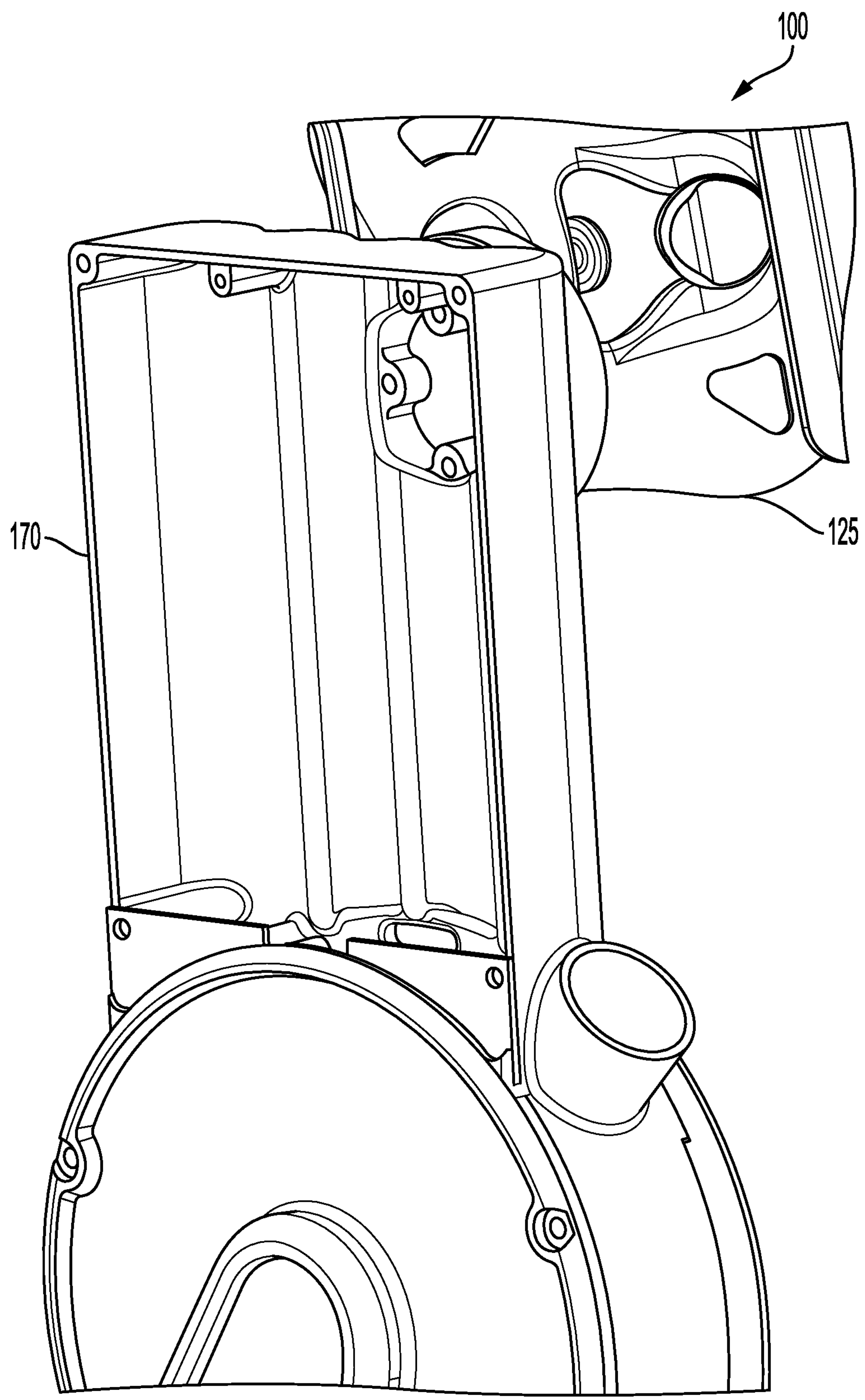
FIG. 25 illustrates a schematic diagram of the exoskeleton and an integrated battery module, according to an embodiment.

FIG. 25 illustrates an integrated battery holder for battery cells 505, in accordance with implementations. The battery holder 170 can be integrated with the exoskeleton 100. The battery holder 170 can form a part of the exoskeleton 100. The battery holder 170 can provide structural support, integrity or functionality to the exoskeleton 100. The battery holder 170 can receive battery cells 505, and couple the battery cells 505 to the battery holder 170. The battery cells 405 can be fixedly attached to the battery holder 170, or the battery cells 505 can be removably attached to the battery holder 170. For example, in the integrated battery configuration, the battery cells 505 couple to the battery holder 170, and the battery electronics, including the battery balancer, can be fixedly coupled to the exoskeleton, for example. However, in the removable battery module configuration, certain battery electronics can be part of the battery module and be removable, such as the battery balancer component, for example.

Figure 26:
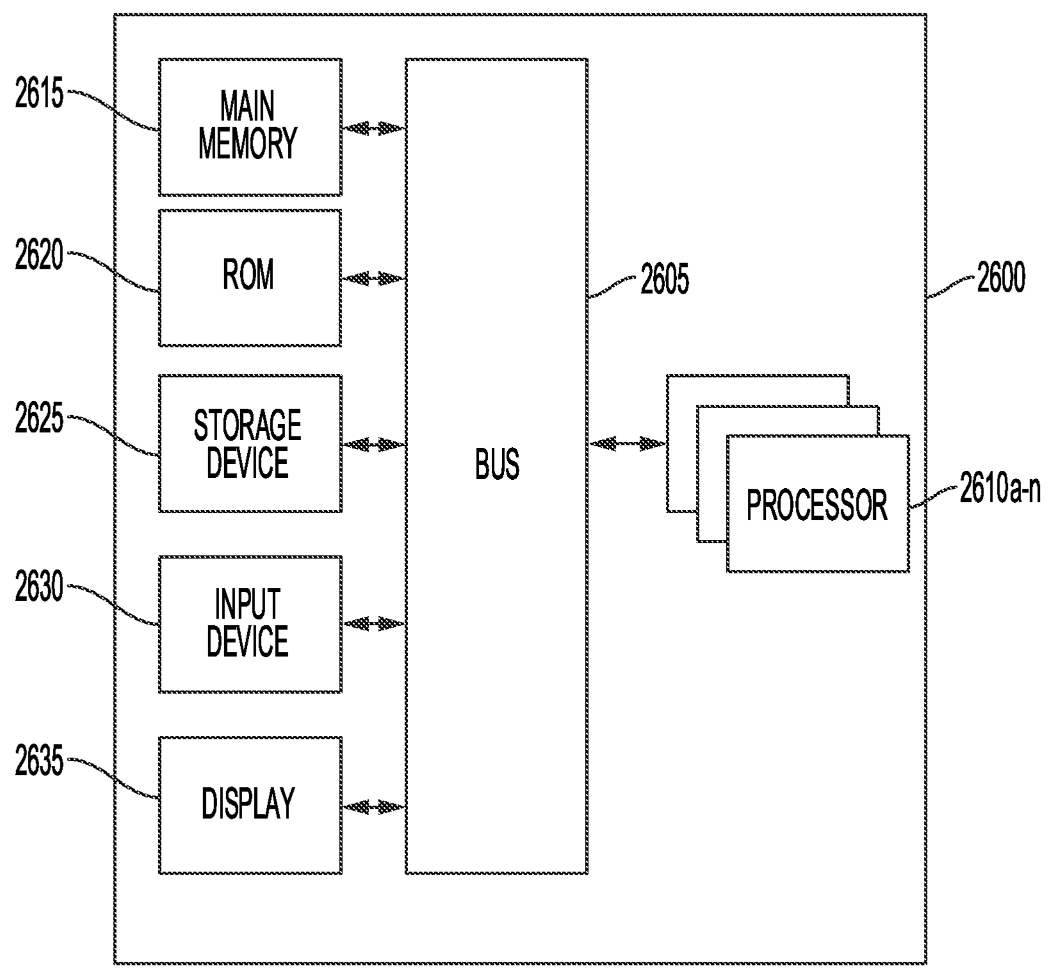
FIG. 26 illustrates a block diagram of an architecture for a computing system employed to implement various elements of the system and methods depicted in FIGS. 1-25, according to an embodiment.

FIG. 26 illustrates a block diagram of an architecture for a computing system employed to implement various elements of the system and methods depicted in FIGS. 1-21, according to an embodiment. FIG. 26 is a block diagram of a data processing system including a computer system 2600 in accordance with an embodiment. The computer system can include or execute a coherency filter component. The data processing system, computer system or computing device 2600 can be used to implement one or more components configured to process data or signals depicted in FIGS. 1-25. The computing system 2600 includes a bus 2605 or other communication component for communicating information and a processor **2610*a-n* or processing circuit coupled to the bus 2605 for processing information. The computing system 2600 can also include one or more processors 2610 or processing circuits coupled to the bus for processing information. The computing system 2600 also includes main memory 2615, such as a random access memory (RAM) or other dynamic storage device, coupled to the bus 2605 for storing information, and instructions to be executed by the processor 2610. Main memory 2615 can also be used for storing time gating function data, temporal windows, images, reports, executable code, temporary variables, or other intermediate information during execution of instructions by the processor 2610. The computing system 2600 may further include a read only memory (ROM) 2620 or other static storage device coupled to the bus 2605 for storing static information and instructions for the processor 2610. A storage device 2625, such as a solid state device, magnetic disk or optical disk, is coupled to the bus 2605** for persistently storing information and instructions.

The computing system 2600 may be coupled via the bus 2605 to a display 2635 or display device, such as a liquid crystal display, or active matrix display, for displaying information to a user. An input device 2630, such as a keyboard including alphanumeric and other keys, may be coupled to the bus 2605 for communicating information and command selections to the processor 2610. The input device 2630 can include a touch screen display 2635. The input device 2630 can also include a cursor control, such as a mouse, a trackball, or cursor direction keys, for communicating direction information and command selections to the processor 2610 and for controlling cursor movement on the display 2635.

The processes, systems and methods described herein can be implemented by the computing system 2600 in response to the processor 2610 executing an arrangement of instructions contained in main memory 2615. Such instructions can be read into main memory 2615 from another computer-readable medium, such as the storage device 2625. Execution of the arrangement of instructions contained in main memory 2615 causes the computing system 2600 to perform the illustrative processes described herein. One or more processors in a multi-processing arrangement may also be employed to execute the instructions contained in main memory 2615. In some embodiments, hard-wired circuitry may be used in place of or in combination with software instructions to effect illustrative implementations. Thus, embodiments are not limited to any specific combination of hardware circuitry and software.

Although an example computing system has been described in FIG. 26, embodiments of the subject matter and the functional operations described in this specification can be implemented in other types of digital electronic circuitry, or in computer software, firmware, or hardware, including the structures disclosed in this specification and their structural equivalents, or in combinations of one or more of them.

Embodiments of the subject matter and the operations described in this specification can be implemented in digital electronic circuitry, or in computer software, firmware, or hardware, including the structures disclosed in this specification and their structural equivalents, or in combinations of one or more of them. The subject matter described in this specification can be implemented as one or more computer programs, e.g., one or more circuits of computer program instructions, encoded on one or more computer storage media for execution by, or to control the operation of, data processing apparatus. Alternatively or in addition, the program instructions can be encoded on an artificially generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate components or media (e.g., multiple CDs, disks, or other storage devices).

The operations described in this specification can be performed by a data processing apparatus on data stored on one or more computer-readable storage devices or received from other sources. The term "data processing apparatus" or "computing device" encompasses various apparatuses, devices, and machines for processing data, including by way of example a programmable processor, a computer, a system on a chip, or multiple ones, or combinations of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a circuit, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more circuits, subprograms, or portions of code). A computer program can be deployed to be executed on one computer or on multiple computers that are located at one site or distributed across multiple sites and interconnected by a communication network.

Processors suitable for the execution of a computer program include, by way of example, microprocessors, and any one or more processors of a digital computer. A processor can receive instructions and data from a read only memory or a random access memory or both. The elements of a computer are a processor for performing actions in accordance with instructions and one or more memory devices for storing instructions and data. A computer can include, or be operatively coupled to receive data from or transfer data to, or both, one or more mass storage devices for storing data, e.g., magnetic, magneto optical disks, or optical disks. A computer need not have such devices. Moreover, a computer can be embedded in another device, e.g., a personal digital assistant (PDA), a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, implementations of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

The implementations described herein can be implemented in any of numerous ways including, for example, using hardware, software or a combination thereof. When implemented in software, the software code can be executed on any suitable processor or collection of processors, whether provided in a single computer or distributed among multiple computers.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

A computer employed to implement at least a portion of the functionality described herein may comprise a memory, one or more processing units (also referred to herein simply as "processors"), one or more communication interfaces, one or more display units, and one or more user input devices. The memory may comprise any computer-readable media, and may store computer instructions (also referred to herein as "processor-executable instructions") for implementing the various functionalities described herein. The processing unit(s) may be used to execute the instructions. The communication interface(s) may be coupled to a wired or wireless network, bus, or other communication means and may therefore allow the computer to transmit communications to or receive communications from other devices. The display unit(s) may be provided, for example, to allow a user to view various information in connection with execution of the instructions. The user input device(s) may be provided, for example, to allow the user to make manual adjustments, make selections, enter data or various other information, or interact in any of a variety of manners with the processor during execution of the instructions.

The various methods or processes outlined herein may be coded as software that is executable on one or more processors that employ any one of a variety of operating systems or platforms. Additionally, such software may be written using any of a number of suitable programming languages or programming or scripting tools, and also may be compiled as executable machine language code or intermediate code that is executed on a framework or virtual machine.

In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other non-transitory medium or tangible computer storage medium) encoded with one or more programs that, when executed on one or more computers or other processors, perform methods that implement the various embodiments of the solution discussed above. The computer readable medium or media can be transportable, such that the program or programs stored thereon can be loaded onto one or more different computers or other processors to implement various aspects of the present solution as discussed above.

The terms "program" or "software" are used herein to refer to any type of computer code or set of computer-executable instructions that can be employed to program a computer or other processor to implement various aspects of embodiments as discussed above. One or more computer programs that when executed perform methods of the present solution need not reside on a single computer or processor, but may be distributed in a modular fashion amongst a number of different computers or processors to implement various aspects of the present solution.

Computer-executable instructions may be in many forms, such as program modules, executed by one or more computers or other devices. Program modules can include routines, programs, objects, components, data structures, or other components that perform particular tasks or implement particular abstract data types. The functionality of the program modules can be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

Any references to implementations or elements or acts of the systems and methods herein referred to in the singular can include implementations including a plurality of these elements, and any references in plural to any implementation or element or act herein can include implementations including only a single element. References in the singular or plural form are not intended to limit the presently disclosed systems or methods, their components, acts, or elements to single or plural configurations. References to any act or element being based on any information, act or element may include implementations where the act or element is based at least in part on any information, act, or element.

Any implementation disclosed herein may be combined with any other implementation, and references to "an implementation," "some implementations," "an alternate implementation," "various implementations," "one implementation" or the like are not necessarily mutually exclusive and are intended to indicate that a particular feature, structure, or characteristic described in connection with the implementation may be included in at least one implementation. Such terms as used herein are not necessarily all referring to the same implementation. Any implementation may be combined with any other implementation, inclusively or exclusively, in any manner consistent with the aspects and implementations disclosed herein.

References to "or" may be construed as inclusive so that any terms described using "or" may indicate any of a single, more than one, and all of the described terms. References to at least one of a conjunctive list of terms may be construed as an inclusive OR to indicate any of a single, more than one, and all of the described terms. For example, a reference to "at least one of 'A' and 'B'" can include only 'A', only 'B', as well as both 'A' and 'B'. Elements other than 'A' and 'B' can also be included.

The systems and methods described herein may be embodied in other specific forms without departing from the characteristics thereof. The foregoing implementations are illustrative rather than limiting of the described systems and methods.

Where technical features in the drawings, detailed description or any claim are followed by reference signs, the reference signs have been included to increase the intelligibility of the drawings, detailed description, and claims. Accordingly, neither the reference signs nor their absence have any limiting effect on the scope of any claim elements.

The systems and methods described herein may be embodied in other specific forms without departing from the characteristics thereof. The foregoing implementations are illustrative rather than limiting of the described systems and methods. Scope of the systems and methods described herein is thus indicated by the appended claims, rather than the foregoing description, and changes that come within the meaning and range of equivalency of the claims are embraced therein.

What is claimed is:

1. An apparatus, comprising:

an exoskeleton wearable on a lower limb of a user, the exoskeleton comprising:

a battery holder, mechanically coupled to the exoskeleton and located at the lower limb of the user, configured to hold a battery in contact with a power connector;

an actuator, mechanically coupled to the exoskeleton, configured to receive power from the battery and generate torque about an axis of rotation of the lower limb.

2. The apparatus of claim 1, comprising:

the power connector comprising a blade connector; and a second power connector comprising a receptacle configured to receive the blade connector absent an exposed cable.

3. The apparatus of claim 2, wherein the blade connector comprises an asymmetric and keyed design.

4. The apparatus of claim 2, wherein the blade connector is recessed within a power connector housing to prevent damage to the blade connector.

5. The apparatus of claim 1, wherein the exoskeleton comprises a shin pad to contact at least a portion of the lower limb of the user, and the battery holder mechanically couples to the shin pad.

6. The apparatus of claim 1, wherein wherein a coefficient of friction between the battery holder and the battery satisfies a threshold to cause a force due to the friction and a force due to gravity to hold the battery in the battery holder.

7. The apparatus of claim 3, wherein the battery is held in the battery holder without a mechanical button or mechanical latch.

8. The apparatus of claim 1, wherein the exoskeleton is wearable on at least one of a foot or ankle of the user.

9. The apparatus of claim 1, wherein the exoskeleton comprises a housing, located on the exoskeleton wearable on the lower limb, containing electronic circuitry, the electronic circuitry to control delivery of power from the battery to the actuator.

10. The apparatus of claim 1, wherein the power connector comprises a serial data communication port to provide information about the battery to one or more processors.

11. The apparatus of claim 1, wherein the exoskeleton comprises a user interface configured to provide an indication of a state of the battery.

12. A system, comprising:

an exoskeleton wearable on a lower limb of a user;

a battery holder, mechanically coupled to the exoskeleton and located at the lower limb, configured to hold a battery in contact with a power connector; and an actuator, mechanically coupled to the exoskeleton, configured to receive power from the battery and generate torque about an axis of rotation of the lower limb.

13. The system of claim 12, comprising:

a serial data communication port to provide information about the battery to one or more processors.

14. The system of claim 12, comprising:

electronic circuitry configured to:

receive a voltage input;

compare the voltage input with a threshold; and wake up, responsive to the comparison, a battery management system of the battery.

15. The system of claim 12, comprising:

the power connector comprising a blade connector; and a second power connector comprising a receptacle configured to receive the blade connector absent an exposed cable.

16. A method, comprising:

providing an exoskeleton wearable on a lower limb of a user, the exoskeleton comprising:

a battery holder, mechanically coupled to the exoskeleton and located at the lower limb of the user, configured to hold a battery in contact with a power connector;

an actuator, mechanically coupled to the exoskeleton, configured to receive power from the battery and generate torque about an axis of rotation of the lower limb.

17. The method of claim 16, comprising:

holding, by the battery holder, the battery using a force due to friction between the battery and the battery holder and a force due to gravity, wherein the battery holder holds the battery without use of a mechanical button.

18. The method of claim 16, comprising:

providing a shin pad to contact at least a portion of the lower limb of the user, the shin pad mechanically coupling the battery holder to the battery holder.

19. The method of claim 16, comprising:

providing, via a user interface, an indication of a state of the battery.

20. The method of claim 16, comprising:

wearing the exoskeleton on at least one of a foot or ankle of the user, wherein the exoskeleton comprises a foot plate in contact with the foot of the user.

* * * * *